United States Patent
Nemenov

(10) Patent No.: US 7,402,167 B2
(45) Date of Patent: Jul. 22, 2008

(54) PORTABLE LASER AND PROCESS FOR PRODUCING CONTROLLED PAIN

(76) Inventor: Mikhail Nemenov, 284 Tyrella Ave. #10, Mountain View, CA (US) 94087

( * ) Notice: Subject to any disclaimer, the term of this patent is extended or adjusted under 35 U.S.C. 154(b) by 361 days.

(21) Appl. No.: 10/790,992

(22) Filed: Mar. 2, 2004

(65) Prior Publication Data

US 2005/0027336 A1    Feb. 3, 2005

Related U.S. Application Data

(60) Provisional application No. 60/451,034, filed on Mar. 3, 2003.

(51) Int. Cl.
*A61N 5/067* (2006.01)
(52) U.S. Cl. .............. 607/89; 128/898; 607/88
(58) Field of Classification Search ......... 128/898; 607/88–94
See application file for complete search history.

(56) References Cited

U.S. PATENT DOCUMENTS

| | | | | |
|---|---|---|---|---|
| 3,900,034 | A * | 8/1975 | Katz et al. | 607/89 |
| 4,854,320 | A * | 8/1989 | Dew et al. | 606/3 |
| 4,966,144 | A * | 10/1990 | Rochkind et al. | 607/89 |
| 5,540,676 | A * | 7/1996 | Freiberg | 606/3 |
| 5,800,481 | A * | 9/1998 | Loos | 607/100 |
| 6,210,882 | B1 * | 4/2001 | Landers et al. | 435/6 |
| 6,233,480 | B1 * | 5/2001 | Hochman et al. | 600/476 |
| 6,267,779 | B1 * | 7/2001 | Gerdes | 607/89 |
| 6,746,473 | B2 * | 6/2004 | Shanks et al. | 607/89 |
| 7,079,900 | B2 * | 7/2006 | Greenburg et al. | 607/54 |
| 2002/0002391 | A1 * | 1/2002 | Gerdes | 607/89 |
| 2002/0099419 | A1 * | 7/2002 | Cohen et al. | 607/46 |

OTHER PUBLICATIONS

Inward currents in primary nociceptive neurons of the rat and pain sensations in humans elicited by infrared diode laser puilses; Greffrath et al.; International Association for the Study of Pain, Sep. 2002.*

(Continued)

*Primary Examiner*—Henry M Johnson, III
(74) *Attorney, Agent, or Firm*—John R. Ross; John R. Ross, III

(57) ABSTRACT

A process and laser system for in vitro and in vivo pain research, pain clinical testing and pain management. In preferred embodiments of the present invention a diode laser operating at a 980 nm wavelength is used to produce warmth, tickling, itching, touch, burning, hot pain or pin-prick pain. The device and methods can be used for stimulation of a single nerve fiber, groups of nerve fibers, nerve fibers of single type only as well as more the one type of nerve fibers simultaneously. The present invention is especially useful for research of human/animal sensitivity, pain management, drug investigation and testing, and psychophysiology/electrophysiology studies. The device and methods permit non-contact, reproducible and controlled tests that avoid risk of skin damage. Applicant an his fellow workers have shown that tests with human subjects with the process and laser of the present invention correlate perfectly with laboratory tests with nerve fibers of rats. The device and the methods can be applied in a wide variety of situations involving the study and treatment of pain. Preferred embodiments of the present invention provide laser systems and techniques that permit mapping and single mode activation of C fibers and A-delta fibers.

18 Claims, 12 Drawing Sheets

OTHER PUBLICATIONS

Clinical application of laser evoked potentials using the Nd:YAG laser ; Lefaucheur et al.; Neurophysiologie Clinique/Clinical Neurophysiology vol. 32, Issue 2 , Apr. 2002, pp. 91-98.*

A Laser Stimulator for the Study of Cutaneous Thermal and Pain Sensations, Meyer et al., Biomedical Engineering, IEEE Transactions on Biomedical Engineering, vol. BME-23, Issue: 1, Jan. 1976.*

Nociceptive masseter inhibitory reflexes evoked by laser radiant heat and electrical stimuli; Ellrich J; Hopf H C; Treede R D Brain research (Netherlands) Aug. 1, 1997, 764 (1-2) p. 214-20.*

Laser Evoked Brain Potentials in the Assessment of Pain: Methods, Applications, Brain Source Analyses: BROMM B (1) Pain Res, 1997, vol. 12,No. 2, p. 41-57.*

J. Mor A Carmon. Laser emitting radiant heat for pain research. 1975, Pain 1 233-37.

R. A. Meyer et al. A laser stimulator for the study of cataneous thermal and sensations. IEEE Trans. On Biomed. Eng. 23, 54-60 Jan. 1976.

T. K. Bauman and M. E. Martenson. Thermosensitivity of cultured trigeminal neurons. 1994 Soc. Neoroscci. (Abstract) 20, 1379 and a cited abstract.

K Jimbor et al. Suppresive effects of low-power laser irradiation on bradykinin evoked action potentials in cultured murine dorsal root gandlion cells. Neuroscience letters 240 (1998) 93-6.

N. Wittenburg and R Baumeister. Thermal avoidance in Caenorhaditis elegants: An approach to the study or nociception. PNAS, neurobiooogy (1999)96, 10477-82.

* cited by examiner

Example of arbitrary shape laser pulse built from short (such as 1 ms) pulses

Example of standard square wave laser pulses:  FIG. 11

A) Single pulses such as: 1 ms – 60 sec

| Power, W | Pulse duration, ms | Irradiated diameter, mm | Energy, mJ | Energy density, mJ/mm2 | Power density, W/mm2 |
|---|---|---|---|---|---|
| 20 | 10 | 1 | 200 | 255 | 25.5 |
| 16 | 20 | 1 | 320 | 408 | 20.4 |
| 10 | 50 | 1 | 500 | 637 | 12.7 |
| 2 | 500 | 1 | 1000 | 1274 | 2.5 |
|  |  |  |  |  |  |
| 10 | 200 | 2.5 | 2000 | 408 | 2.0 |
| 3.5 | 300 | 2.5 | 1050 | 215 | 0.7 |
| 2 | 500 | 2.5 | 1000 | 204 | 0.4 |
|  |  |  |  |  |  |
| 1.5 | 1000 | 3 | 1500 | 212 | 0.2 |
| 1.2 | 2000 | 3 | 2400 | 340 | 0.17 |
| 1.1 | 20000 | 5 | 22000 | 1121 | 0.06 |

| Number of Pulses | Power, W | Pulse Duration, ms | Irradiated area, mm | Interval between pulses, sec | Energy, mJ | Energy density, mJ/mm2 |
|---|---|---|---|---|---|---|
| 100 | 2.5 | 50 | 2 | 0.35 | 125 | 39.8 |
| 25 | 5 | 300 | 7 | 3 | 1500 | 39 |
| 100 | 10 | 50 | 1 | 60 | 500 | 636.9 |
| 40 | 1.5 | 80 | 2 | 0.15 | 120 | 38.2 |

PORTABLE LASER AND PROCESS FOR PRODUCING CONTROLLED PAIN

Applicant claims the benefit of Provisional Patent Application Ser. No. 60/451,034 filed Mar. 3, 2003. This invention relates medical instruments and processes and in particular to instruments and processes for producing pain.

FIELD OF INVENTION

BACKGROUND OF THE INVENTION

Chronic Pain is a Most Serious Problem

Chronic pain places an enormous toll on the human society. Pain syndromes affect more than 30 million Americans per year, costing more than 100 billion dollars in medical expenses and lost work, in addition to the immeasurable expense of human suffering. Unfortunately, currently available means of assessing the pain of these patients are limited in their predictive value in terms of directing treatment regimes.

Prior-Art Research and Medical Devices for Producing Pain

Contemporary basic pain research has a number of significant problems and serious limitations. One of these problems is the inability to create repeatable and reproducible pain stimuli that permit selective activation of particular types of nerve fibers. Progress in pain research has been retarded because of the lack of adequate equipment to test pain sensing nerve fibers in a variety of clinical conditions. In order to obtain statistically proven data during the testing of analgesic drugs in every phase of drug development including clinical trials, it is desirable (and may be necessary) to have objective parameters to estimate the level of pain. If pain could be quantified, this could enormously shorten the time of clinical trials and diagnostics needed to demonstrate statistically significant clinical results.

Pain stimulators currently available on the market in general do not provide adequate stimuli or suffer other deficiencies such as:
  low level of repeatability
  low rate of heating
  inconvenient heat delivery
  lack of quantitative sensory effects
  lack of ability to objectively estimate degree of pain
  lack of ability to produce of single (mono-modal) skin pain sensations as well as other mono-modal skin sensations
  lack of ability to selectively assess pain mediated by the activation of different classes of pain sensing nerve cells Radiant heat stimulators are used in animal pain research. These devices are limited by accuracy of intensity and produce relatively large spots. Heating rates are generally too low to accurately measure very short response times. Some prior art pain stimulators are described in the following patents which are incorporated herein by reference: U.S. Pat. No. 5,191,896, U.S. Pat. No. 6,248,079, and U.S. Pat. No. 5,025,796.

Ion Channel Research

An important area of nerve research concerns the study of ion channels in the membranes of nerve cells that open and close to regulate nerve impulses including those signaling pain. For heat pain research with nerve cells in vitro, such as experiments concerning ion channels, heat stimuli are typically delivered to cells with a standard perfusion bath apparatus or a Peltier contact heating device. With these devices rates of temperature change are low requiring heat durations on the order of seconds for substantial temperature rises. These instruments can not achieve measurable thermal stimulation of cells in milliseconds. A significantly more rapid stimulus would permit measurements of opening and closing of these channels in response to heat, thereby providing significantly greater insight into the molecular mechanisms of channel activation and regulation.

Use of Lasers

It is known to use lasers for producing pain. Lasers operating at various infrared wavelengths have been utilized in pain research. Lasers provide advantages as compared to radiant heat sources. These are:
  high rate of heating,
  heat for some wavelengths can be delivered by optical fiber, and
  ease of directing laser energy to specific locations.

One problem with many laser sources is that skin damage occurs before or simultaneously with the feeling of pain. Another problem is that laser pulses may produce double sensations that can induce potentials on one type of fiber by suppressing interaction mechanisms between other nerve fibers, for example in the spinal cord. This is most frequently seen for laser pulse duration of more than 100 ms. It is known that lasers operating in the range of 980 nm can produce pain in skin tissues. Photons at this wavelength penetrate to about 3.8 mm through skin tissue.

Nociceptors: A-Delta Fibers and C Fibers

Basic research in pain, analgesia and pharmacology has been accelerating over last several years. One of the results of this work has been the clear demonstration of the differential involvement of different pain sensing nerve cells (called nociceptors). There are two main classes of pain sensing nociceptors in the skin and other peripheral tissue: myclinated A-delta nociceptors and un-myclinated C nociceptors. These nerve cells may also be called nerve fibers. Sensations evoked by activation of these two different nociceptor types are quite distinct. A-delta fiber mediated pain is typically described as sharp, or piercing. C fiber mediated pain, on the other hand, is usually described as burning or aching. There is also a dramatic difference in the latency to pain after activating these two nociceptor types. For example, a rapid pin-prick to a foot can produce two distinct pain sensations: first, a sharp pain which ends when the pin is removed, followed by a second, burning sensation which may be felt well after the needle has left the skin. The first pain is mediated by A-delta nociceptors, and the second pain is mediated by C fiber nociceptors. Thus, activation of these two nerve types has a different meaning to the body. Numerous physiological, anatomical, and pharmacological distinctions have also been described as being distinct between these two nerve types. For example, morphine is much more effective in inhibiting C fiber mediated pain than A delta fiber mediated pain. Included among these is the finding that, with a constant stimulus, such as a wound, A-delta nerve cells respond robustly at first, but then rapidly become quiescent. On the other hand, C fibers, with the same stimulus, continue to fire continuously. A delta fibers are usually responsible for mediating of sharp pin prick pain and C fibers for warmth sensations and hot/burning pain.

Some chronic pain syndromes, e.g., diabetic neuropathic pain, may be mediated primarily by C fiber activations. Microneurographic studies in patients with painful diabetic neuropathy demonstrate clear increases in sensitivity of unmyelinated (C) nociceptors. Similarly, a preponderance of pain experienced by patients with fibromyalgia is generally associated with C fibers. Conversely, other painful conditions, such as some polyneuropathies and some dental pains appear to be predominately mediated by A-delta nociceptor activation. Thus, the ability to accurately evaluate single C or A-delta fiber function would be useful in both in diagnosis of these diseases as well as for following patient progress. The ability to study a single types of responses (i.e., a C fiber or an A-delta fiber individually) is referred to as "single mode" investigations or "monomodal investigations.

Applicant's Prior Pain Research

Applicant has been conducting pain research using lasers since 1993. In that year he and others successfully developed a protocol for inducing of pricking pain with Cu vapor laser and warmth sensation and hot pain with YAG:Nd laser. During these experiments, a He—Cd laser and a laser diode was also evaluated. The laser diode that was applied had only 600 mW output power and this power level was too small to product effective results. The paper was published in 1994: M. I. Nemenov, L. G. Gladusheva, E. M. Tsirulnikov, I. G. Andreeva. "Thermal and Skin Pain Sensations Due to Laser Irradiation". SPIE Proceeding, v.2323, p. 537-538, (1994). In 1995, Applicant published a draft calculation of a simple thermal model that compared laser heating and estimates parameters of an ideal pain stimulator. This paper was reported at Laser School in Sicily: M. I. Nemenov, E. M. Tsirulnikov, et al. "Investigation of Skin Sensitivity due to Visible and Near Infrared Laser Radiation", Biomedical Optical Instrumentation and Laser-Assisted Biotechnology, Erice, Sicily, Nov. 10-22,1995, v. E325, NATO ASI book series, p.73-80 (1996). Applicant with others conducted additional laser pain experiments in May of 1997 and results were reported in International Workshop: Semiconductor and solid state laser in medicine '97 in St. Petersburg: M. I. Nemenov, E. M. Tsirul'nikov, "Skin Sensation and Laser Radiation as Universal Stimuli", Technical Digest of International Workshop: Semiconductor and Solid State Laser in Medicine 97 and R. A. Suris, M. I. Nemenov. Semiconductor Lasers: Advantages to Medicine., Proceeding of International Workshop: Semiconductor and Solid State Laser in Medicine 97 Russia, St. Petersburg, May 24-25, 1997, pp 3-10; M. I. Nemenov, E. M. Tsirul'nikov, "Laser Tissue Interaction and Skin Sensations", The Fifth Congress of Scandinavian Society for Laser Therapy, Arhus, Denmark, Apr. 4-5, 1997, Technical Digest. Brief result of laser diode stimulator and possible advantages were reported at Second Workshop: Semiconductor and Solid State Laser in Medicine '98 in St. Petersburg: M. I. Nemenov, E. M. Tsirul'nikov "Semiconductor Lasers in Pain and Sensory Research". Technical Digest of the Second International Workshop Semiconductor and Solid State Lasers in Medicine '98, St. Petersburg, May 28-30, 1998. In June of 1998, Applicant successfully developed laser based stimulating device and tested them in Aalborg University. Applicant presented this work in September 1998, showing a new prototype of a 980-nm diode laser device based on 20 W laser module coupled with optical fiber of 420 microns diameter. This work was published: M. I. Nemenov, L. Arendt-Nielsen, "Laser Diodes in Pain research (preliminary study)" Technical Digest of International Symposium on Biomedical Optics Europe '98, Stockholm, Sweden, September 1998, 3570-50. Applicant present the results of research in 1998-2000 research in the following publications: M. I. Nemenov, V. G. Zaitcev, and J. Mikkelsen, "Limitations of Laser Application in Pain Research". Proceeding of 19th World Pain Congress, August 1999, Vienna, No. 317 (abstract); J. Nielsen, M. Nemenov et al, Laser diode: "Pain Threshold and Temperature Distribution in Human Skin". Proceeding of 19th World Pain Congress, August 1999, Vienna, No. 79 (abstract); M. I. Nemenov, P. F. Bradley et al, "Quantitative Measurement of Laser Evoked Painful Sensations". 20th Annual Meeting of American Society for Laser Medicine and Surgery, Reno, Nev., Apr. 5-9, 2000 J. "Laser Medicine and Surgery" (abstract); M. I. Nemenov, W. Greffrath, S. Schwarz, H. Vogel, V. Zaitcev, R.-D. Treede and "A Laser Diode Stimulator for the Study of Cutaneus Pain Sensations", "Laser Evoked Potentials, and Thermal Responses of Primary Nociceptive Neurons" and The 5th International Symposium on Pediatric Pain, London, UK, 18-21 Jun. 2000 (Abstract).

What is needed is a better product and process for producing controlled selective quantitative pain. Specifically, there is a need for the development of a commercially viable infrared laser stimulator that will allow mapping and differential assessment of pain signals carried by C fibers and A-delta fibers.

SUMMARY OF THE INVENTION

The present invention provides a process and laser system for pain research, pain clinical testing and pain management. A diode laser may be used to produce warmth, tickling, itching, touch, burning/hot pain and pin-prick pain. The device and methods of the present invention can be used for stimulation of a single nerve fiber, groups of nerve fibers, nerve fibers of single type only as well as of different types of nerve fibers simultaneously. The present invention is especially useful for research of human or animal sensitivity, pain management, drug investigation and testing, and in psychophysiology and electrophysiology studies. The device and methods permit non-contact, reproducible and controlled tests that avoid the risk of skin damage. Applicant and his fellow workers have shown that tests with human subjects utilizing embodiments of the present invention correlate perfectly with laboratory test with nerve fibers of rats. The device and the methods can be applied in a wide variety of situations involving the study and treatment of pain. Preferred embodiments of the present invention provide laser systems and techniques that permit mapping and single mode activation of C vs. A-delta fibers.

BRIEF DESCRIPTION OF THE DRAWINGS

FIG. 11 shows examples of single square wave pulses.

DETAILED DESCRIPTION OF PREFERRED EMBODIMENTS

Diode Laser System at 980 nm

Figure 1:
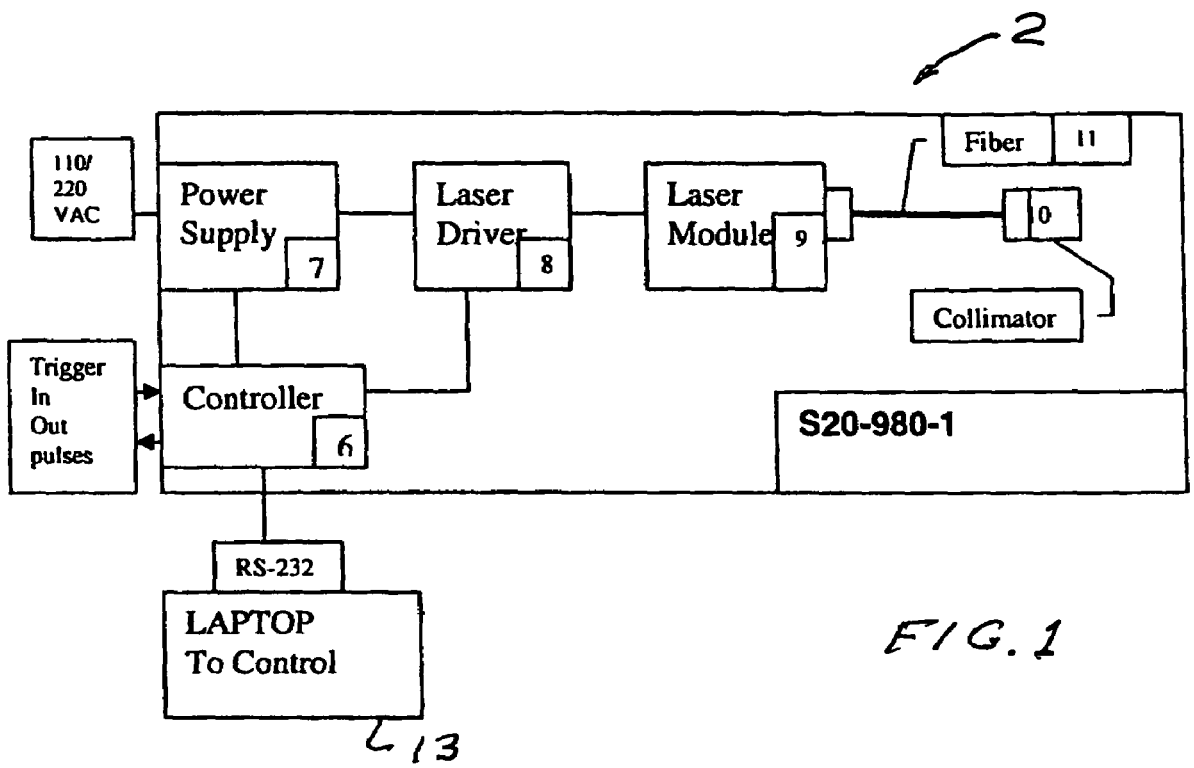
FIG. 1 is a block diagram of a preferred embodiment of the present invention.

A preferred laser system for practicing the present invention is shown in FIG. 1 and is described below. It is a GaInAs/GaAs diode laser system available turnkey as Model No. S20-980-1 form Apollo Instruments Inc. with office located in 18019 Sky Park Circle, Suite F, Irvine, Calif. 92614. The laser system 2 includes: laser module 9 capable of producing up to 30 Watt laser beam as continuous wave or in tailored pulses. The system also includes laser driver 8, laser controller 6, power supply 7, and collimator 10. In addition, the system also includes a 5-mW red aiming diode laser (not shown). The output beam is fed into a fiber coupling and fiber connector with an efficiency of ~80%. The preferred optical fiber has a core diameter 100 microns and numerical aperture of 0.22-11. The laser is operated at wavelength of 980 nm for most experiments of the type described herein. However, other wavelengths in the range of 200 nm to 1.9 microns are available by changing diodes. The laser may also be used as a pump beam to produce other wavelengths. The laser system includes personal laptop computer 14 programmed to provide the following functions:

1) Standard square wave laser pulses:
    A) Single pulses such as: 1 ms-60 sec,
    B) Repeatable pulses such as 1 ms-60 sec with intervals pulses of 10 ms-2000 sec.
2) Arbitrarily shaped laser pulses built from short (such as 1 ms) closely spaced (such as 1 ms intervals) pulses. An arbitrary shape pulse could be single or repeatable. An example is twenty ms 0.5-Watt pulses followed by ten ms 0.75-Watt pulses followed by ten ms 1 Watt pulse followed ten ms 1.5 Watt pulses. Such an arbitrary pulse shape could be useful for experiments to determine the speed at which pain signals travel through particular nerves.

Pulse shapes are discussed in more detail below and are described in FIGS. 10 through 15B.

Advantages of the Present Invention

Some of the uses and advantages that the present invention provides are listed below:
  (a) many types pain research humans, animal and an ion channels of cells may be conducted,
  (b) a great variety of pulse shape for activation of A-delta fibers in the range of 20 to 300 ms,
  (c) monomodal pin-prick type pain from threshold to tolerance level without generation of skin lesions.
  (d) mapping of location of nociceptors and skin receptors with a resolution of better than 0.1 mm on the surface and better than 0.05 mm in terms of depth in the skin
  (e) an easy measurement of spatial summation of pricking and burning pain and warmth sensations thresholds in the range of diameters from 0.1-100 mm,
  (f) easy timed measurement of thresholds of pricking and burning pain and warmth sensations in the range 10 ms-20 second,
  (g) reproducible differential activation of C vs. A delta fibers and temperature sensitive ion channels with standard deviation of less than 12%,
  (h) reproducible monomodal warmth sensation stimulation,
  (i) reproducible monomodal burning/hot pain stimulation,
  (j) direct differential measurement of speed conductivity of A delta and C fibers,
  (k) direct test of type of pain/sensation mechanisms (cortical, spinal, peripheral) by application of two optical fiber probes to the same dermatome with different offset (latency) times, (For example, because of difference in the activation/inactivation characteristics of C and A delta fibers, the use of two stimulating probes in the same dermatome of patient/volunteer allow for assessment of the neurological area where disturbances in sensory function originate.)
  (l) controllable heating of tissue with adjustable pulse shape,
  (m) direct activation of ion channels in membranes of isolated cells with spatial resolution up to 0.01 mm and temporal resolution up to 1 ms,
  (n) a diagnostic test of threshold of pain/sensation, temporal and spatial summation of thresholds and pain/sensations to determine of normal and abnormal responses,
  (o) reproducible stimulation and offset measurements of oro-facial areas of cutaneous nociceptors and receptors of humans and animals,
  (p) behavioral tests of rats, mice and monkeys,
  (q) psychophysiological test of humans,
  (r) heat controlled activation of nerve fibers, cells, ion channels,
  (s) selective activation of at least A delta and C fibers cells and ion channels by selection or/and control ramp and shape of heating and cooling, size of irradiated (heated area), location of irradiated area, depth of heating. Depth of heating is selected by changing of lasing wavelength of laser diode (800 nm-1.900 micrometer) and beam size and will depends on type of skin (color, area) or color of cells. Heating rate controlled by measurement temperature on the surface of skin or cell and adjusted by tuning the lasing power or/and pulse duration. The heating control could be provide directly by temperature feedback loop or by using empirically determined standard setting for different skin types, (t) investigation of the interference of different or the same types of sensations (activations) by application the same or different stimuli to the same area with tunable time delay and amplitude, (u) increasing of power for pulse duration of 50-150 ms from 0.5 W with step of less than 0.2 W for diameter of irradiation area 0.5-2 mm inducing clear monomodal pin prick pain and selective activation of A delta fibers in humans as well as in animals. An exception is the orofacial area where some times A delta terminals are absent in humans or/and animals, (v) increasing the pulse duration from 300 ms to 20 sec with a power level of around 1.5 W and diameter of irradiation area between 5 mm-15 mm leads to induction of clear monomodal C fiber hot pain that may or may not follow a warm sensation, and (w) increasing the power for pulse duration of 400-500 ms and diameter of irradiated area 3-5 mm may induce clear monomodal C fiber hot pain or clear monomodal warmth sensation.

Alternative Laser Systems

In another preferred embodiment of the invention a 980-nm laser system is assembled from components available from component suppliers as follows:

Laser Module:
1. Single laser diodes 980 nm are available from JDS Uniphase, Corp. office located in 1768 Automation Parkway San Jose, Calif. 95131,
2. SDL-6380 A, L2, output power 4 W, emitting area 100 microns coupled to standard multimode optical fiber 100/125 microns with numerical aperture (NA) 0.22 by 1.1.7 Fiber coupler, part number 9003.002, LIMO are available from Lissotschenko Mikrooptik GmbH, with offices located in Bookenburgweg 4-8 44319 Dortmund, Germany.
3. Laser diode bars are available from Coherent Inc office located in 5100 Patrick Henry Drive, Santa Clara, Calif. 95054,
4. CW bars part number 1015325 type B1-98-30C-19-30-A coupled to standard multi-mode fiber 100/125 microns with numerical aperture (NA) 0.22 or laser diode CW bars SPL MA98-F are available from OSRAM Opto Semiconductors office located 3870 North First Street San Jose, Calif. 95134
5. Laser modules where single laser diodes or laser bars are coupled to 100/125 microns fiber together with vision pilot lighting are available from the following sources: Laser Modules: Model F20-980-1, Apollo Instruments, Inc. office located in 18019 Sky Park Circle, Suite F, Irvine, Calif. 92614 or/and Model HLU15F100-980, LIMO—Lissotschenko Mikrooptik GmbH, office located in Bookenburgweg 4-8 44319 Dortmund, Germany or/and PUMA-20, QPhotonics L.L.C. office located in 21 Pepperwood Drive, Chesapeake, Va. 23320, Model LASS 20 M, LASMED LLC, 284 Tyrella Ave Suite 10, Mountain View, Calif.
6. Laser diodes are controlled by driver current that transform input voltage amplitude to current and apply this current to laser diode module. The following laser driver are available on the market for 20 W laser diode models: P40-808-6, D-560, Apollo Instruments Inc., LDD-50/100, Lumina Power Inc., or/and 7701A, Analog Modules Inc, LDD50 LIMO—Lissotschenko Mikrooptik GmbH; LASS 20 M, LASMED LLC.

The free tip of the optical fiber can be linked to a collimator to avoid differences in power density as the distance between skin and collimator is changed. The ideal collimator should have a minimum beam size 1-1.5+/−0.1 mm within a range of 10-40 mm and a tunable beam size of 1.5-15 mm. The type of collimator that is available on market permits the decreasing of beam divergence and keep the diameter of spot 1+/−0.1 mm in working distance ~5 mm. Collimators are available (OEM LC-1—fiber connected collimator) from Multimode Fiber Optics Inc. office located in 9A Great Meadow Lane, East Hanover, N.J. 07936 or F230 series of collimators available from Thorlabs Inc., with office in Newton, N.J.

The NA×D is a constant for geometrical optics, where NA—numerical aperture (divergence of beam in radians), D—diameter of core fiber or beam after fiber. Therefore, an increasing of diameter of beam from 0.1 mm to 1 mm permits a decrease in the beam divergence 10 times. This permits to have a beam diameter of +/−0.1 mm for range of 5 mm after collimator.

The above laser systems can produce laser pulses with durations of 1 ms-200 sec with an accuracy of +/−1 ms and power of 50 mW-20 W with an accuracy of +/−0.5%. The several models of controllers as well as turnkey systems that include a laser diode module, laser driver and program controller that comply with these specifications are available on the market: S20-980-1, Apollo Instruments Inc; BWF4, BWTEK office located in 825 Dawson Drive, Suite 1 Newark, Del. 19713. (OEM), as described above. The controller preferably also controls laser current and the temperature of laser diodes inside the laser module and monitors lasing power and set up power and control power and state (switch on/off) of the pilot (aiming) beam.

A set of algorithms are preferably developed to permit use of laser diode system for selective activation of C and A delta fibers. The set may be developed and applied based on laser manufacturers instructions such as those provided with the laser module of DLR series of IPG Photonics Corporation, office located in Oxford, Mass.

Low Cost Testing

An inexpensive way to selectively stimulate A-delta and C fibers with a laser is to use single a laser diode coupled to 100/125 or 60/125 fiber. For example, the SDL-6390-L3 of JDS Uniphase laser with output power of 5 W per 100/125 microns fiber is currently available. It has only one laser diode. The 5 W SDL6390-L3 can stimulate C fibers and wide range of pulse duration and beam size and permit stimulation of A delta fibers in the range of 100-150 ms, and beam size ~0.5-1.0 mm.

Laser Configurations

A 980-nm diode laser 28 of the type described above can be arranged in a variety of configurations for laboratory research, clinical research, clinical testing or treatment. Some of these configurations are described in FIGS. 1A through 5.

Figure 1A:
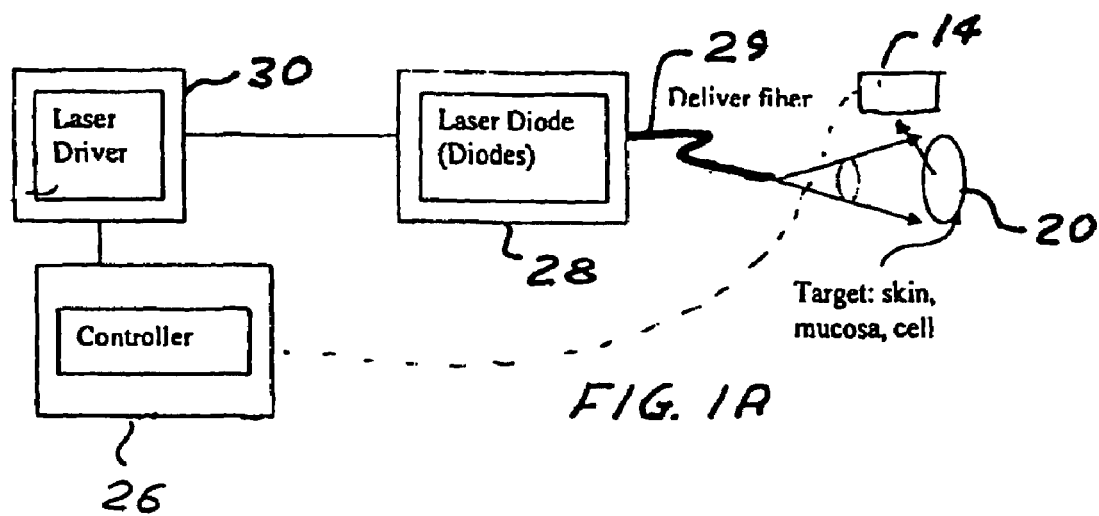
FIGS. 1A, 1B and 1C show various types of laser delivery systems.
Figure 1B:
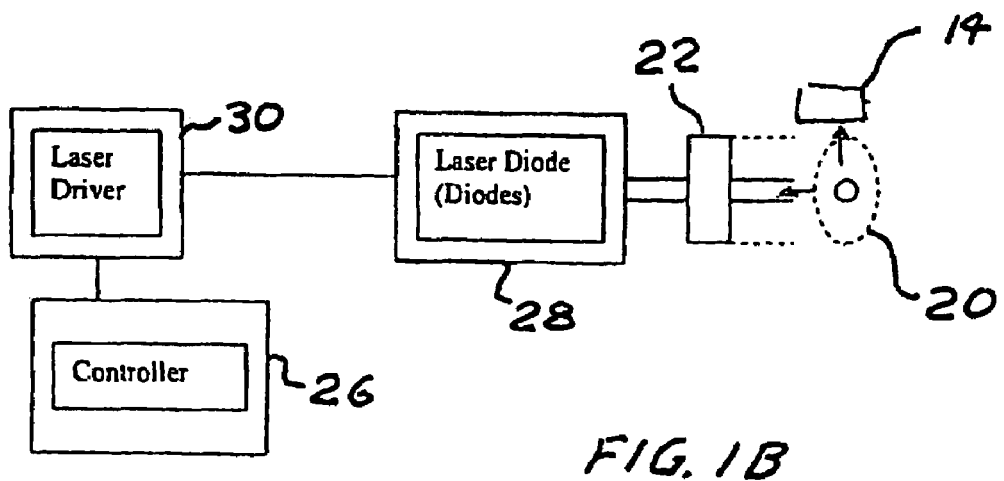
Figure 1C:
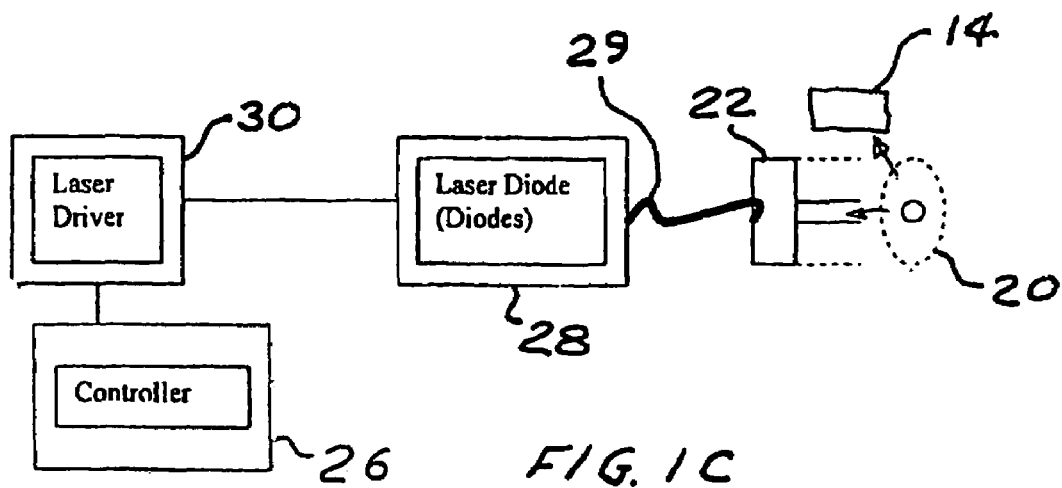

FIG. 1A shows a system in which a fiber optic 29 is used to deliver laser pulses from diode laser 28 to skin surface 20 with the temperature of the surface being monitored by infrared sensing camera 14 that provides a feedback signal to controller 26 for synchronization of stimulation scan and image recording and monitoring of time interval between applied laser pulse and muscle reflex. FIG. 1B is similar to FIG. 1A except the laser pulses are delivered as a collimated beam using lenses 22. FIG. 1C combines the pulse delivery features of FIGS. 1A and 1B.

Figure 2A:
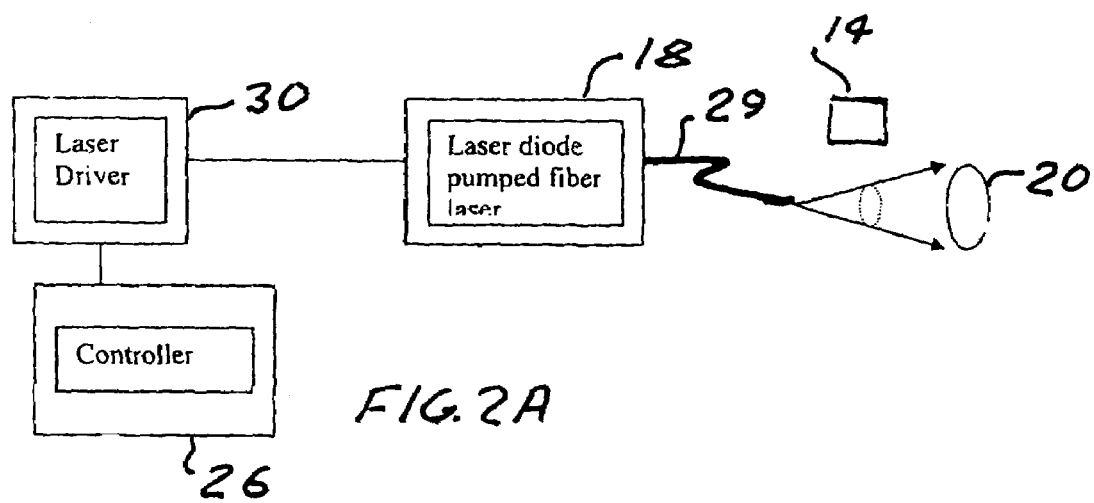
FIGS. 2A-2B show two additional types of delivery systems.
Figure 2B:
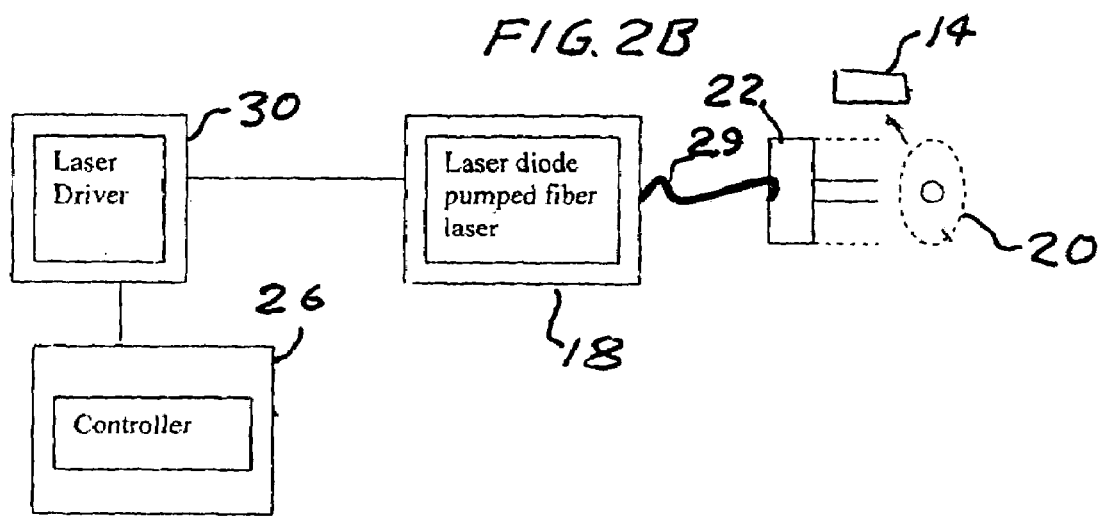

In FIG. 2A an active erbium doped fiber 18 is pumped by the 980 nm diode laser system 30 to produce 1450 nm laser pulses at the output of the fiber. The preferred fiber 18 is single mode fiber with core diameter 5-15 microns, NA 0.11-0.22. The 1450 nm pulses are used to illuminate skin surface 20 through optical fiber 29 for applications where this longer wavelength pulse energy is desired. This setup is also good for doing activation of ion channels in laboratory experiments. In FIG. 2B the output from laser diode vumped fiber laser 18 and optical fiber 29 is collimated with a tunable collimator 22 to control the diameter of the beam within a range of 1 to 15 microns. An infrared sensing camera 14 in both eases monitors the irradiated spot 20 and records reflexes of the subject.

Figure 3:
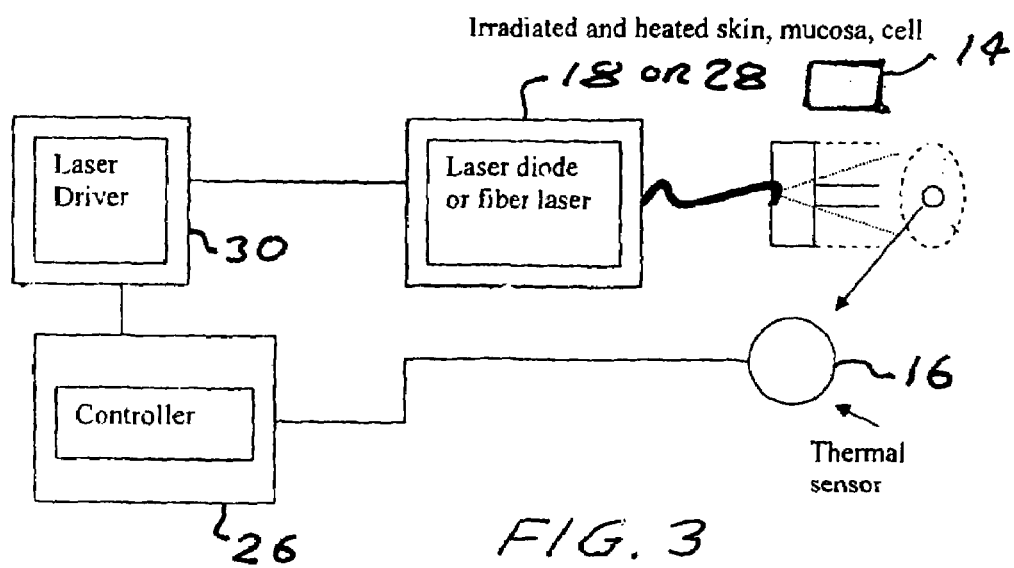
FIG. 3 shows a light delivery system with temperature feedback loop from an infrared thermal sensor.
Figure 4:
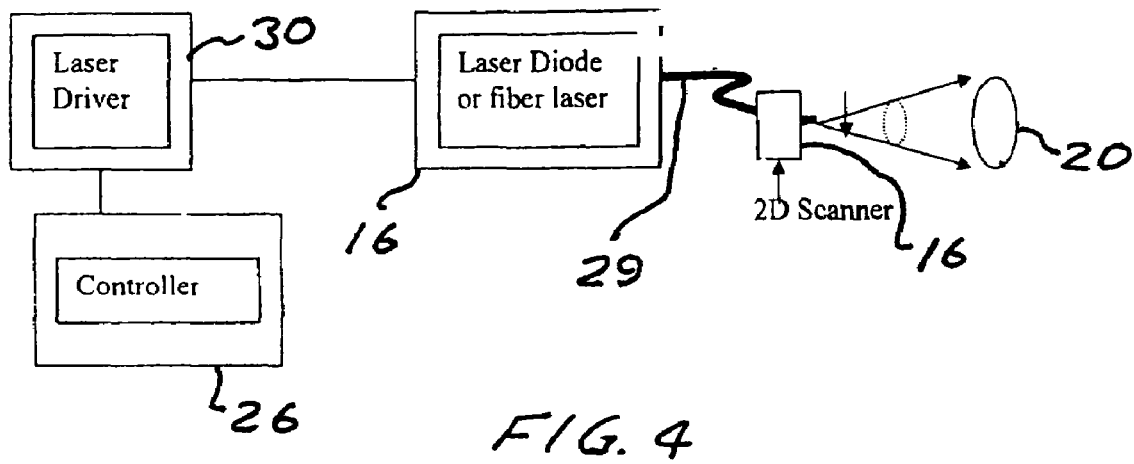
FIG. 4 shows a two-dimensional scanner to map test locations on skin surface.
Figure 5:
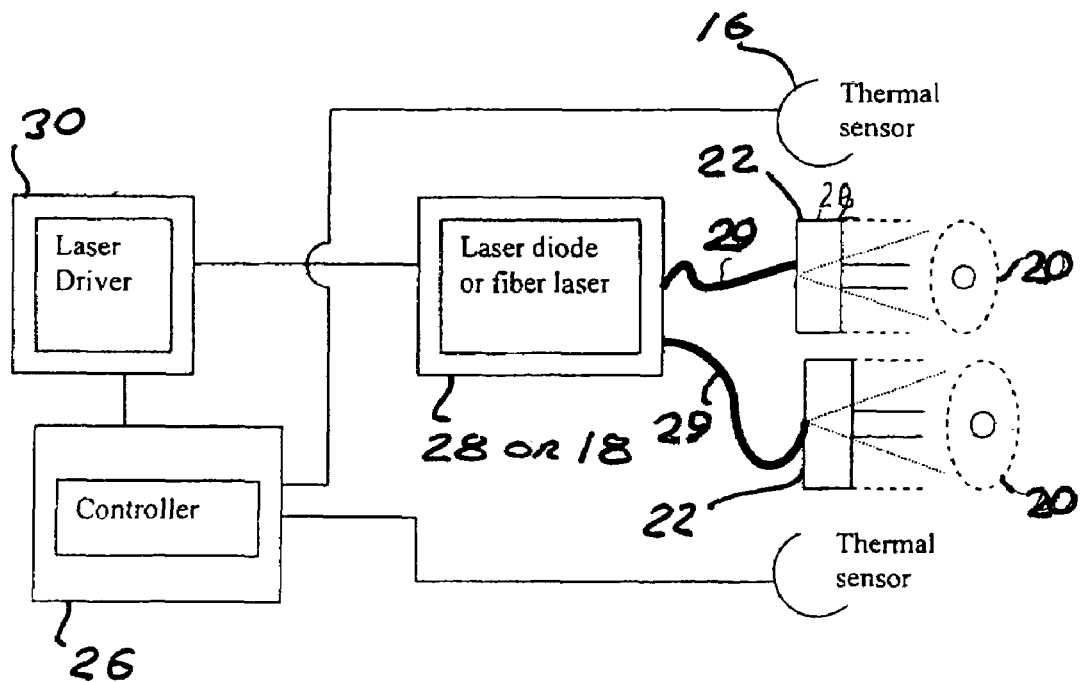
FIG. 5 shows two light delivery systems (two laser probes) to directly measure the speed of conduction of nerve fibers.

In FIG. 3 temperature feedback is provided with thermal infrared sensor 16 that can be used to control the temperature—time profile with a precision of less than 1 millisecond and 1 degree centigrade. In FIG. 4 a two dimensional scanner 16 is used to provide a precise illuminated pattern on a target area 20. Scanners such as Model SCANcube.RTM. 7 (available from SCANLAB AG with offices in Cincinnati, Ohio) provide scans with a precision of about 5 mrad. In FIG. 5 a single laser (that could provide either 980-nm pulses or 1450-nm pulses) is used to illuminate two regions at the same time or with tunable time delay. In another embodiment a single controller controls two completely separate laser systems each with its own laser driver. This could be important in experiments when measuring response times to separate pain events.

Figure 6A:
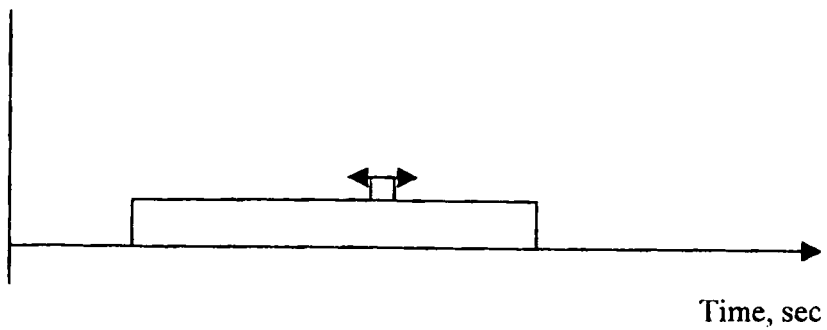
FIGS. 6A and 6B shows a technique for testing nerve response using specially tailored laser pulse shapes.
Figure 6B:
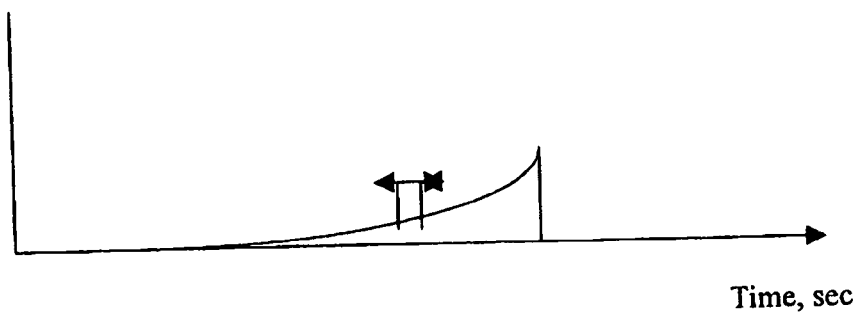

FIGS. 6A and 6B show the type of pulse power profile that is available with the laser system first described above. FIG. 6A shows power vs time and FIG. 6B shows temperature vs time. The purpose here is to gradually heat the skin to a temperature just below the pain threshold and then provide a short pulse to exceed the threshold. With this technique the time of the short pulse providing the threshold energy can be measured with precision, and compared to a reflex or a measured nerve signal to accurately determine nerve transit times and other important information regarding the functioning of the nerves.

Figure 7A:
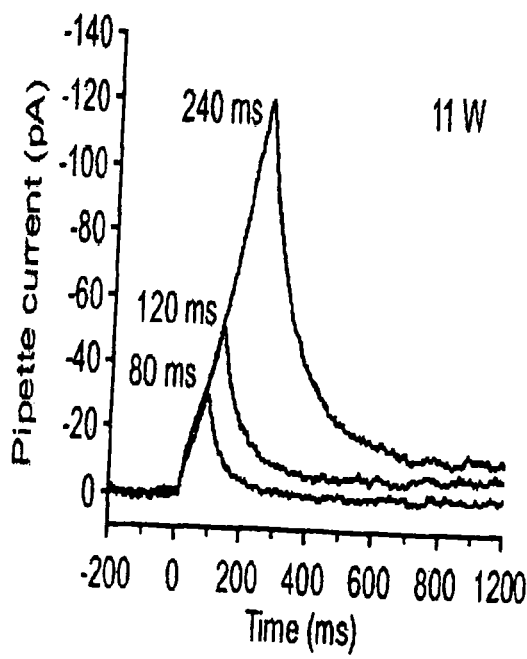
FIGS. 7A and 7B shows traces of heat sensitive neurons for various power and pulse durations.
Figure 7B:
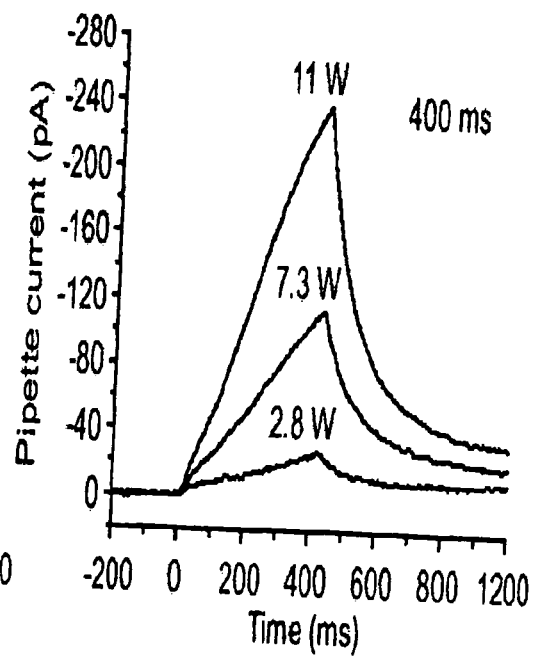
Figure 8A:
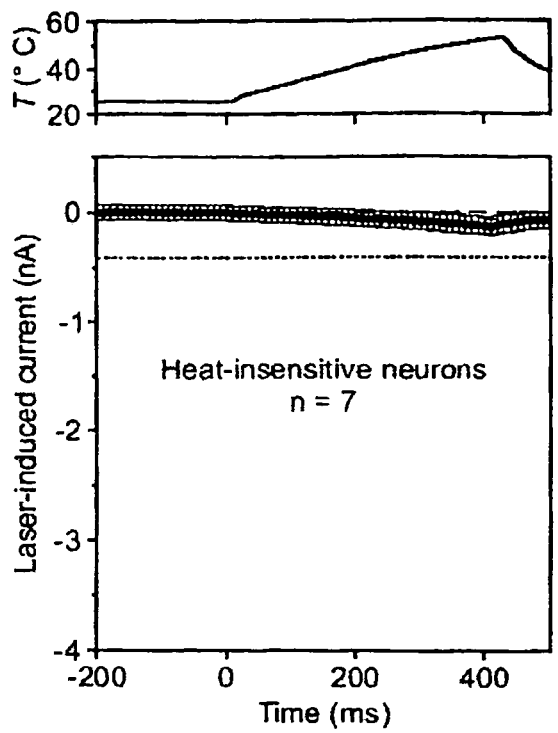
FIGS. 8A and 8B show activation of heat sensitive neurons vs neurons that do not respond significantly.
Figure 8B:
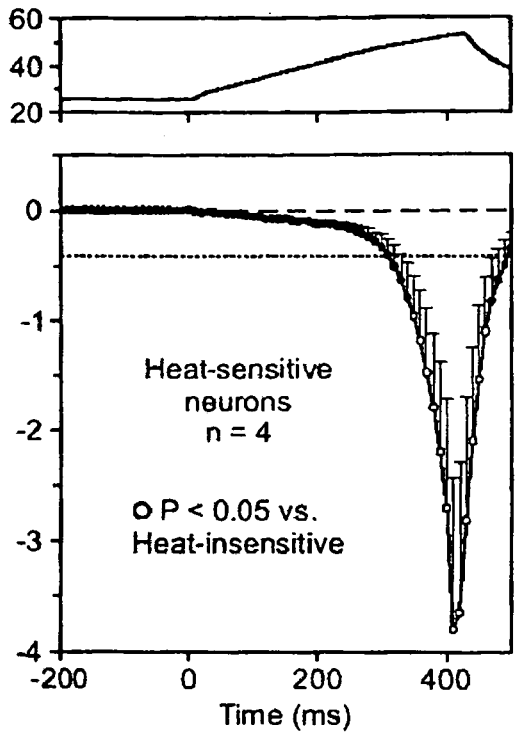

FIGS. 7A and 7B show heat induced current in a heat sensitive cell from a dorsal root ganglion of a rat. The heat was provided with 1.2-mm diameter, 980-nm, 11-Watt pulses for the time periods indicated. In FIG. 7A the maximum pulse duration was 240 ms, and for the FIG. 7B graph the maximum pulse duration was 400 ms. FIG. 8A shows the results of tests on a neuron that was not heat sensitive. Heat resulted in only a very slight current. FIG. 8B however shows the effect of applying heat in the same amount and under the same conditions to a heat sensitive neuron from a dorsal root ganglion of a rat.

Figure 9:
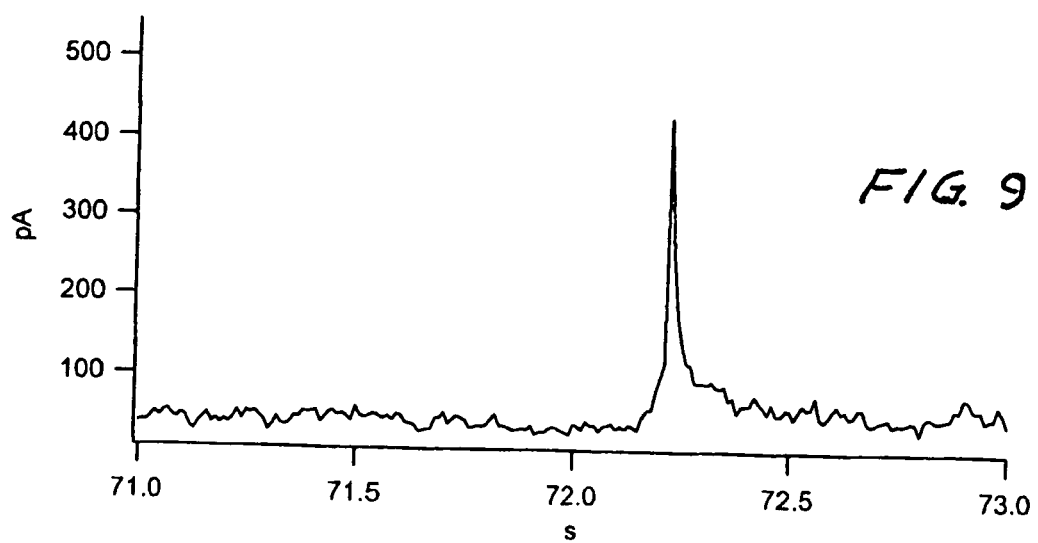
FIG. 9 shows show results of laser heat induced activation of heat sensitive ion channels.
Figure 10:
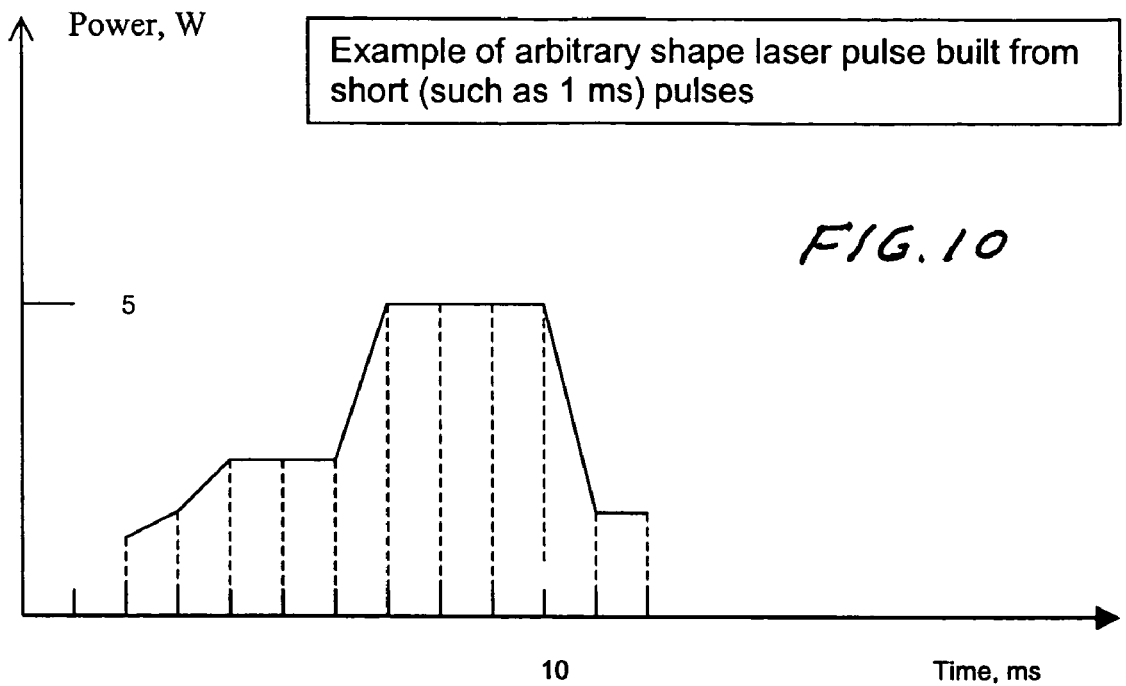
FIG. 10 shows an arbitrary 10 ms pulse shape built from 1 ms pulses.

FIG. 9 shows results of ion-channel experiments performed by Applicant with the above-identified 980-nm laser system. The laser heat induced current of inside-out membrane patches from VR1-expressed HEK293 cells. The cells were stimulated by laser light and electro-physiological responses were recorded using a standard patch-clamp protocol. The laser stimulus evoked TRPV 1-mediated currents based on their characteristic current-voltage profile and the absence of such responses in cells not expressing VR1. A trace of the response is provided in FIG. 9. The size of membrane patches was around 10 microns, pulse duration 100 ms, and the size of irradiated area 100 microns.

EXAMPLES OF PAIN TESTING PROCEDURES

Example 1

Pin Prick Pain to Activate A Delta Fibers

It is well known that for heat induced simulation of prick-pain stimulation the temperature of the skin has to be more than 46-48 C. degree and the ramp of heating has to be over 70-100 C. degrees per second. However, these data were based on pulse durations of more than 300 ms. To the best of Applicant's knowledge, here are not any data in the literature relating absolute temperature and ramp of heating for stimuli duration less than 300 ms. The best, simplest protocol, to access A-delta nociceptors and evoked monomodal pin prick pain is the following:

The best laser set up parameters for lasing of 980 nm:
Pulse duration: 50-150 ms,
Beam size: 0.5-2 mm
Power: 2-20 W
Density of Energy Range: 1-4 mJ/mm$^2$ An example of practical realization of the combination of pulse duration, beam size and pulse power for threshold pin prick pain stimulation is shown in Table 1:

TABLE 1

Example of Threshold of Single Pin Prick Pain Stimulation (A delta fibers). Irradiated Spot Diameter 0.8 mm, Glabrous Skin

| Pulse, ms | POWER, W | Energy, mJ | Peak Temperature, C. | Energy Density mJ/mm$^2$ | Power Density W/mm$^2$ |
|---|---|---|---|---|---|
| 50 | 9.5 | 475 | 73 | 945 | 18.9 |
| 100 | 4.5 | 450 | 62.5 | 896 | 9.0 |
| 150 | 3.2 | 480 | 58 | 955 | 6.4 |
| 200 | 2.76 | 552 | 57 | 1098 | 5.5 |
| 300 | 2.5 | 750 | 54.8 | 1492 | 5.0 |

The experiment consisted of the following actions:
1) Collimated beam with a diameter of 2 mm, within a range of power of 5.0-10.0 W and a pulse duration of 100 ms is applied to investigated area of skin to determine the individual sensitivity and to map the location of A delta nociceptors. The pulse power is increased from 5 W with step of 0.5 W until first sensation is evoked. After that the pulse power is fixed and the irradiated spot is scanned Within XY frame 5 mm×5 mm to find the location of a nociceptor. Pulse power is applied for each new location—the spatial step is around 0.5 mm for fingertips. The inter-stimulus time is 20 sec.
2) When the location of appropriate spot is determined, the size of collimated beam is adjusted to 1 mm, duration of pulse set up to 50 ms and pulse power is increased from 2 W until the threshold level is achieved. After that, either the power is increased up to tolerance level of pain or power could be increased by 20% (the estimated tolerance level is about 20%-30% above the power to induced threshold pain) and psychophysiology or electrophysilogy testing could be done.
3) The step of increasing of power is within the range of 0.1 Watt-1.0 Watt with pulse duration of 300 ms-50 ms.
4) For determining temporal summation curve (Power of Pain Thresholds vs. Pulse Duration), step 2) is repeated with successively longer pulse duration until 200-300 ms is reached (steps of pulse duration 50 ms) or until the first type of evoked sensation with increasing of power will be warmth, burning/hot pain or any other sensation but not pin prick pain.

5) The time interval between applied laser pulses should be more than at least 20 sec-200 sec to avoid an average heating of skin or until induced sensation/pain completely disappeared.

Figures 12, 13:
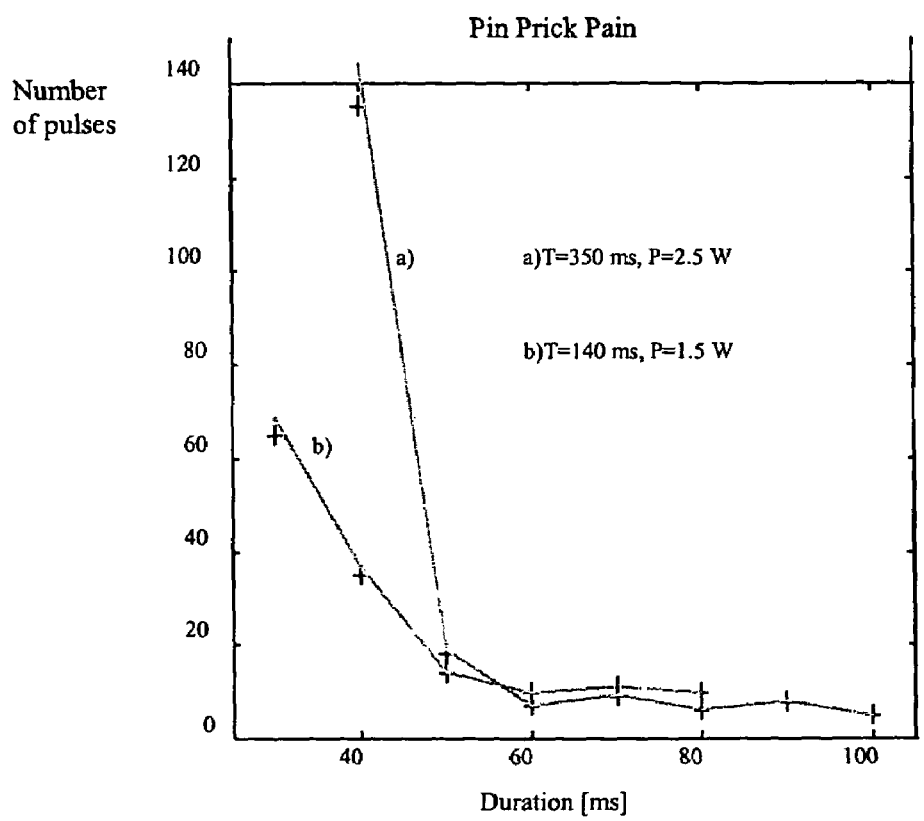
FIG. 12 shows examples of repeating pulses with intervals between them.
FIG. 13 shows simulated threshold pin-prick values for 2.5 Watt and 1.5 Watt pulses with variable numbers of pulses and variable pulse durations.

6) For determining the number of pulses that evokes threshold of pin-prick type pain; square waved pulses within a range of pulse duration of 10-300 ms and interstimulus delay of 0.1-3 sec are applied. Examples of repetitive pulse application for A delta stimulation are shown in FIGS. 12 and 13.

7) In the case of chronic pain syndromes diagnosis there could be differences between normal skin sensitivity and tender areas. For example, for fibromyalgia syndrome the actions 1-4 are repeated for normal and tender areas before and after treatment.

8) In the case of testing of topical anesthetics or an analgesic drug actions temperature of surface skin of investigated area is monitored and data before and after application of topical anesthesia or an analgesic.

9) The pain thresholds as well as tolerance levels are individual, but suggested actions allow to avoid temporal skin irritation and skin damage because the pain threshold power level for 980 nm lasing is lower than the damage level.

Figure 16A:
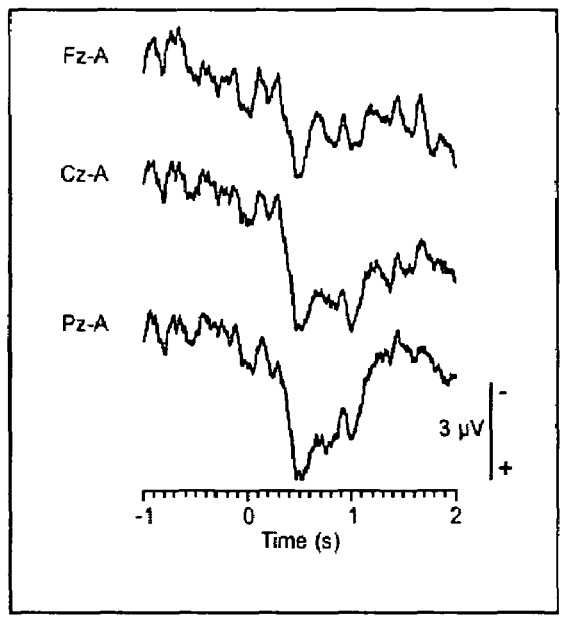
FIGS. 16A and 16B show evoked potentials test data and location of brain wave detectors for pin-prick type pain.
Figure 16B:
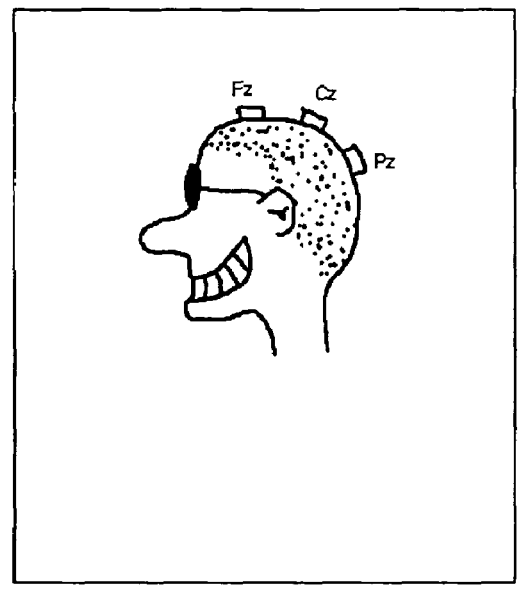

10) Electrophysiology—Recording Evoked Cortical Potentials: the pulse duration in the range 50-150 ms is selected with power accordingly measured in step 4). The power is adjusted individually in the level between pain threshold and tolerance level. Trigger pulses, synchronized with laser pulses are applied in electroencephalographic recording protocol. The result of recording of A delta fibers (pin prick pain) then the area of hand were stimulated with repetitive laser pulses 5.4 W, 80 ms and interstimulus interval 6 sec are shown in FIG. 16A, the location of electrodes for cortical evoked potentials recording are shown in FIG. 16B.

Example 2

Protocol of Selective Stimulation of Single Warmth Sensation or/and Single Hot pain, Activation of C Fibers Warmth Sensation Stimulation The best laser set up parameters for laser at 980 nm:
Pulse duration: 300 ms to 20 s
Beam size: 3-15 mm
Power: 0.3-10 W 1) Collimated beam with diameter 5 mm, power 1 W and pulse duration 5 sec is applied to investigate area of skin to determine the individual sensitivity of C nociceptors. The lasing is stopped when patient or volunteer report feeling either warmth or hot (burning) pain. The duration of applied pulse is measured. The procedure is repeated 2-3 times and after which the obtained pulse duration is used for the investigation of other areas. Every next pulse is applied to new area of skin if pain or other sensation has not disappeared.

2) The expected pulse duration is between 300 ms and 5 sec. A 300 ms power is increased with step of 0.2 W until the appropriate sensation appears. If the sensation doesn't occurred, then pulses with a duration of 5 sec are applied with increasing of power.

3) The inter stimulation time is at least 20 sec or until the pain sensation has disappeared.

4) For measurement of the Wind Up Effect, the area of stimulation is changed for each successive pulse if pulses applied are separated 2-10 sec.

5) Spatial summation curve: Power density of threshold of warmth or pain vs. Size of irradiated spot. Measurement size of irradiated spot is adjusted to 5 mm, 10 mm and 15 mm and actions 1-2 are repeated for each size with the same selected pulse duration.

6) For measurement of temporal summation curve (Power of Pain Thresholds vs. Pulse Duration) the action 2) is repeated with successive pulses. Pulse power is increased in 0.2 W steps. Expected pulse durations 300 ms-20 sec.

7) The time interval between applied laser pulses has to be more than 3-20 sec to avoid an average heating of skin and skin irritation. Exception is Wind Up Effect where indication of state of skin is subjective rating of pain level and monitoring of surface skin temperature.

Figure 14:
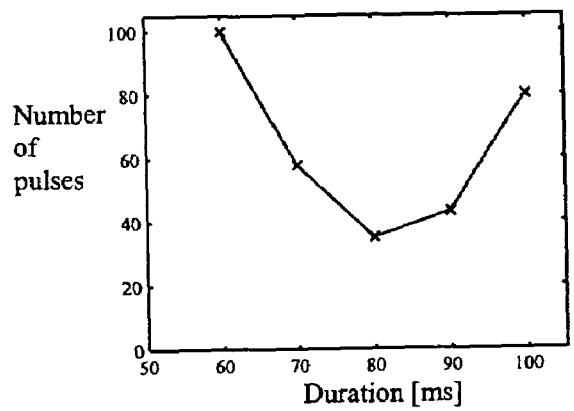
FIG. 14 shows burning pain thresholds with pulse power of 2.5 Watt with variable numbers of pulses and variable pulse durations.
Figure 15A:
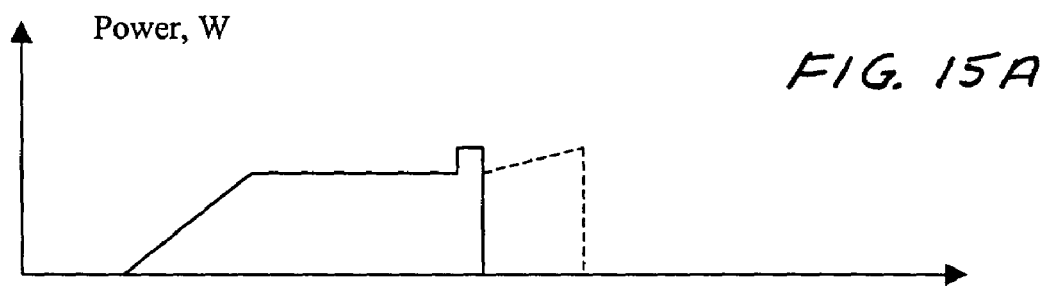
FIGS. 15A and 15B show a preferred tailored pulse for measuring of speed conduction of nerve fibers.
Figure 15B:
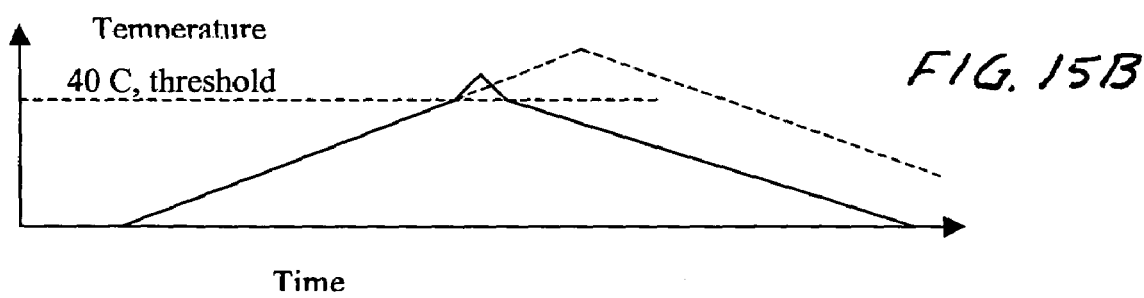

8) For determining of the number of pulses that evoked threshold of hot/burning pain in accumulation of heat the square waved pulses within a range of pulse duration of 10-300 ms and interstimulus delay of 0.1-3 sec are applied. The examples of repetitive pulse application for C delta stimulation are shown in FIG. 14.

9) In the case of chronic pain syndromes diagnostics, there are differences between normal skin sensitivity and tender areas for example for fibromyalgia syndrome, the actions 5 and 6 are repeated for normal and tender areas before and after treatment.

10) In the case of testing of topical anesthecs or an analgesic drug actions, temperature of surface skin of investigated area at which pain occurs is monitored and data before and after application of topical anesthesia or a analgesic drug is obtained.

11) The pain thresholds as well as tolerance level are individual but suggested actions allow to avoid temporal skin irritation and skin damage because the pain threshold level for 980 nm is lower than skin damage level.

12) Electrophysiology—Recording Evoked Cortical Potentials: the pulse duration in the range 300-400 ms (up to 2 sec) is selected with accordingly power measured in step 4) if they are. The power is adjusted individually in the level between pain threshold and tolerance level. Trigger pulses, synchronized with laser pulse are applied to electroencephalographic protocols. The jitter from pulse with duration of 300 ms-2 sec could not resolve the time delay between even pulses applied to hand and shoulder for a very tall subject. To solve this problem two optical fiber probes method (see FIG. 5) and signal pulse method (see FIGS. 6A,B and FIGS. 15A, B) were applied, to measure the time delay between two identically stimulated areas. The time delay was measured by delay time between brief trigger pulses.

Example 3

Example of Application of Protocol Example 2 for Healthy Volunteer

The best laser set up parameters for laser at 980 nm:
Pulse duration: 300 ms to 20 s,
Beam size: 3-15 mm
Power: 1-10 W
Density Energy Range 9-140 mJ/mm2

TABLE 2

Example of threshold Hot Pain and Warmth Stimulations

| Type of sensation | Pulse duration, ms | Area size, mm2 | Power, W | Energy, mJ | Energy Density, mJ/mm2 | Power Density, W/mm2 |
|---|---|---|---|---|---|---|
| warmth | 300 | 38.5 | 4.7 | 1410 | 36.6 | 0.122 |
| warmth | 300 | 176.6 | 5.8 | 1740 | 9.8 | 0.033 |
| warmth | 1300 | 12.7 | 1.1 | 1430 | 112.6 | 0.087 |
| Hot Pain | 300 | 38.5 | 5.8 | 1740 | 45.2 | 0.151 |
| Hot Pain and warmth | 1300 | 19.6 | 2 | 2600 | 132.7 | 0.102 |

Example 4

Group Testing of A Delta Fibers (Application of Protocol Example 1 for Healthy Volunteer and Pain Patient. (The Following is a Description a Typical Test Procedure Utilizing the Present Invention)

Step 1 Preparing volunteer for test. The volunteers were asked to respond to stimuli after each stimulus was applied, and describing the level and type of evoked sensation, location of sensation, how long the sensation lasts, whether the sensation was single (monomodal) or if more than one sensation were evoked by stimulation.

Step 2 The level of power of laser was adjusted to skin type of volunteer and irradiated spot was selected as close as possible to A-delta receptors.

Collimated beam with diameter 2 mm, within range of power 5.0-10.0 W and pulse duration 100 ms is applied to investigated area of skin to determine the individual sensitivity and to map the location of A delta nociceptors. The power is increased with step 0.5 W until the first sensation is evoked. After that, the pulse power is fixed and the position of the irradiated spot is scanned (tuned) within an XY frame 5 mm×5 mm to find the location of the nociceptor and pulse power is applied for each new location with spatial steps of around 0.5 mm for fingertips. The inter-stimulus time was at least 20 sec. The first appeared sensation was rated by the volunteer as barely pricking pain without any other sensations of warmth or hot pain.

Step 3

After the location of receptors were determined, the summation curve—Power of Pain Threshold vs. Pulse Duration were measured by the following procedure: collimated beam was adjusted to 1 mm, duration of pulse set up to 50 ms and pulse power was increased from 2 W until volunteer reported about first appeared sensation. Afterwards, power was increased until volunteer reported that sensation became clearly painful but decreasing of power of stimulus on 5-10% lead the disappearance of pain. Afterward, the power threshold was measured for 50 ms pulse duration was increased by step 50 ms and procedure measurement of threshold was repeated. The increment of power was 0.1 W.

Step 4

The healthy volunteer was tested with pulse durations from 50 ms to 300 ms and beam size of 1 mm. The volunteer reported what around 200-300 ms, he felt on the same level of power firstly warmth and after that pricking pain but for pulses within range 50-150 ms, only single (monomodal) pricking pain was discerned. The sensations were sharp and disappeared in a few seconds after stimulation. The next stimulus was applied not earlier than 20 sec or after the disappearance of painful sensation of previous stimulus.

Step 5

To measure the tolerance level of pain the level of the power was increased more than threshold level with increment of 0.1 W until volunteer reported that his tolerance level of pain had been reached. The procedure of Step 3 was repeated. The volunteer rated his tolerance level as 10 and his threshold level of pain as 1.

Step 6

The threshold of pin prick pain of healthy volunteer were measured in 20 minutes after topical analgesic (capsaicin) was applied on skin. The Steps 2, 3, 4 were repeated.

Step 7

To determine a difference in pain threshold and summation curve between healthy volunteer and chronic pain patient the Steps 1-4 were repeated with patient with chronic hypersensitivity. The result of measurement are shown in Table 3

Step 8

The level of skin irritation was measured by repetition of stimulation until redness of skin appeared for skin of healthy volunteers for stimulus duration of 150-300 ms and was recalculated for pulse durations of 50 and 100 ms. The Power level evoking skin irritation is shown Table 3.

As it is shown in Table 3, there is enough room to measure dependence of analgesic action between skin damage power level and initial pain threshold of pin prick pain. The shape of summation curve as well as pain thresholds allow to to determine the hypersensitive area of skin of chronic pain patient and test of selective action (A delta vs C fiber) of analgesic as well as diagnosing of that type of fiber is responsible for conducting of pain of patients.

TABLE 3

| Pluse Duration, ms | Power of Pain Thresholds of Healthy Volunteer, W | Power of Pain Tolerance of Healthy Volunteer, W | Power of Skin Irritation, W | Power of Pain Thresholds of Healthy Volunteer (Capsaicin), W | Power of Pain Threshold of Chronic Pain Patient with Hypersensitivity, W |
|---|---|---|---|---|---|
| 50 | 9.5 | 11.9 | 16.6 | 14.8 | 7 |
| 100 | 4.5 | 5.6 | 7.9 | 7.0 | 3.5 |
| 150 | 3.2 | 4 | 5.6 | 5 | 2.5 |
| 200 | 2.8 | 3.5 | 4.8 | 4.3 | 2.2 |
| 300 | 2.5 | 3.1 | 4.4 | 3.9 | 2.2 |

Example 5

Comparison of Chronic Pain Patient to Healthy Volunteer for Stimulation of C Fibers—Example Application of Protocols 2

Subjects: A chronic pain patient with hypersensitivity and a healthy volunteer were tested. Both subjects gave informed consent and the experiments were approved by the local institutional review board. The hairy skin of left hand was used for both volunteers. In preparing the subjects testing, they were asked to respond orally immediately after they perceived any threshold sensation and/or to interrupt lasing pulse by pressing STOP button. They then described the level and type of evoked sensation, location of sensation, how long the sensation lasted, whether the sensation was single (monomodal) sensation or if there were more than one evoked sensations by a single stimulation. Afterwards, the threshold pulse was applied 3 times to different areas with interval of ~3 min or after the previous sensation (pain) had disappeared. The appearance redness was an indication of skin irritation.

Step 1 To test duration of pulse that evoked threshold warmth sensation only, the output power was set to 1.5 W, beam size adjusted to 5 mm. The pulse was applied to the skin. When the volunteer reported warmth (pain) sensation the lasing was stopped. The measured threshold pulse durations accordingly were 1300 ms for hot pain for the healthy volunteer, 800 ms hot pain for the healthy volunteer affected topical capsaicin (capsaicin decreases the thresholds of warmth sensation and hot/burning pain) and 910 ms hot pain thresholds for the volunteer with the hypersensitivity. The pulse duration for tolerance for hot pain was 2000 ms. Other studies have shown that redness (skin irritation) only occurs when pulse is extended to 3000 ms.

The laser radiation was stopped by volunteer. The volunteer used the other hand to push the "stop lasing" button when he perceived the sensation. When this button was pushed the command "stop lasing" was activated, duration of applied pulse was measured and it was indicated on the screen of PC connected to the device by RS232 interface.

For the double-checking of reflex time of volunteer, a infra-red CCD camera (Sony) instead infrared thermal camera (14) FIGS. 1A-1C was applied to monitor the irradiated skin and reflex time. This method allowed to measure the real reflex time without time of delay related of individual reaction of volunteers. For tested volunteers the pulsed durations accordingly were: 1270, 650, 770 ms. This method also allowed to monitor the size of irradiated spot directly by infra red lasing as opposed to use the aiming beam. However, there was not found any differences between the diameter aiming beam and the diameter acting infra red lasing beam of irradiated spot. Accuracy of beam size measurement was +/−0.50 microns.

Step 2 To measure the speed conductivity of C fiber alternatively of two probe method power which evoked hot pain sensation for pulse a duration of 300 ms was determined. This pulse duration is short enough to use it for measurement of speed conductivity by electroencephalographic recording of cortical evoked potentials. The output power was set up 1 W, spot size 7 mm with an increment of power was selected 0.1 W. The volunteer was asked to report the threshold of pain, skin sensation tolerance.

Example 6

Activation of Heat Sensitive Ion Channels of Vanilloid Receptors

For this experiment membrane patches are derived from transfected mammalian cells expressing VR1. Experiments are carried out with human embryonic kidney (HEK293) cells expressing the rat VR1 cDNA (Caterina M J, Schumacher Mass., Tominaga M, Rosen T A, Levine J D, Julius D. The capsaicin receptor: a heat-activated ion channel in the pain pathway. Nature 1997; 389:816-824; Tominaga M, Caterina M J, Malmberg A B, Rosen T A, Gilbert H, Skinner K, Raumann B E, Basbaum A I, Julius D. The cloned capsaicin receptor integrates multiple pain-producing stimuli. Neuron 1998; 21:531-543)

Cells are plated on glass cover slips for whole-cell patch-clamp recording procedures or for obtaining excised membrane patches, as previously described by the Chuang (Chuang, H., Prescott, E. D., Kong, H., Shields, S., Jordt, S. E., Basbaum, A. I., Chao, M. V., and Julius, D. (2001) Bradykinin and nerve growth factor release the capsaicin receptor from $PtdIns(4,5)P_2$-mediated inhibition. Nature 411: 957-962). Once high resistance seals to the membrane and stable recordings had been obtained, the laser was positioned close to the cell or excised patch so as to deliver a brief (10-100 mS) pulse. Laser-evoked membrane currents were recorded and analyzed with standard packages (PClamp, Axon Inst.). Current-voltage traces and blockade by VR1 antagonists (capsezapine and ruthenium red) were used to assess the identity of the evoked currents. Negative controls to assess background currents were performed with HEK293 cells expressing other, non-heat-sensitive ion channels.

Figure 17A:
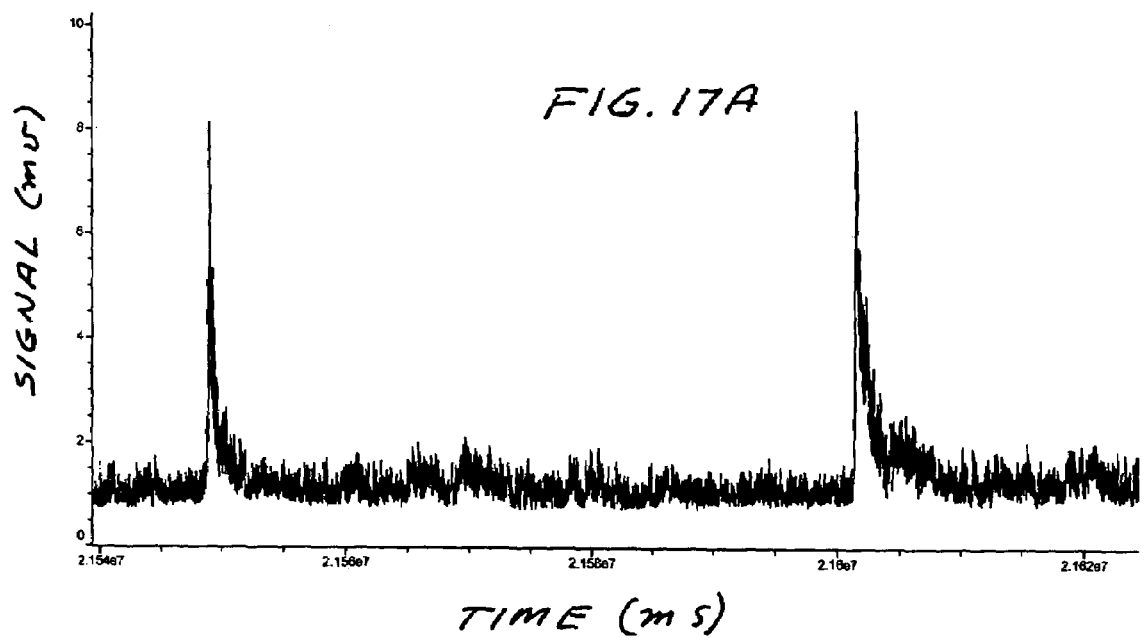
FIGS. 17A and 17B show results of ion channel experiments.
Figure 17B:
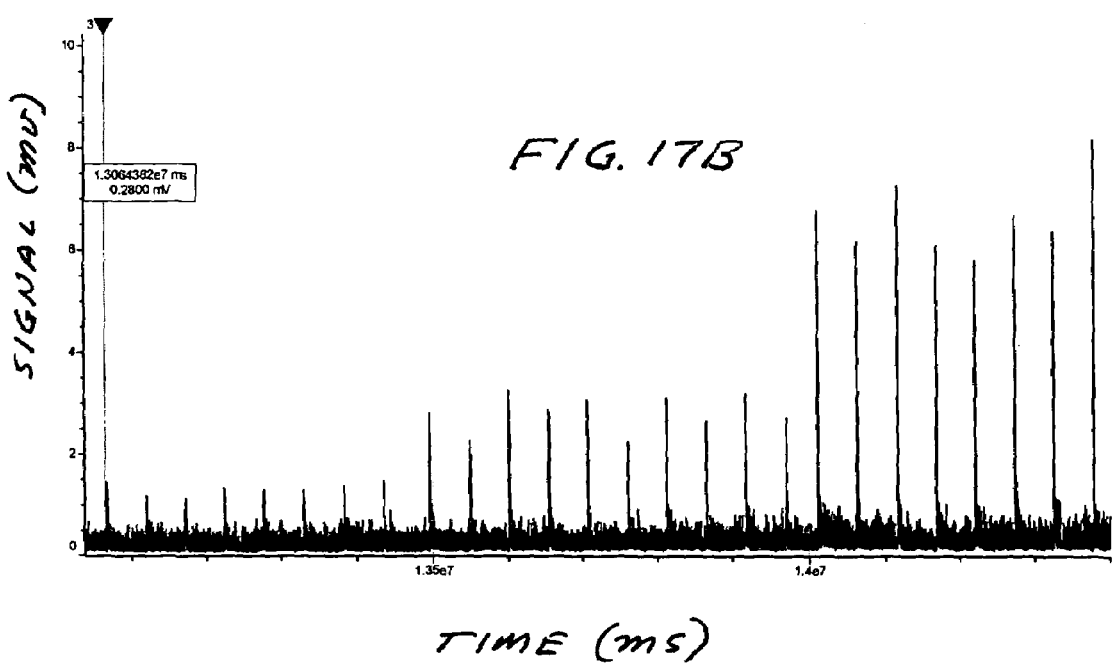

The free 100/125 microns tip of the optical fiber of laser stimulator with an output power of 5 W was used. The distance between membrane patches fixed on pipette and tip of optical fiber was 50 microns. Three pulse powers were applied: 3 W, 4 W, 5 W. Each power set was applied with inter stimulus delay of 10 sec and a pulse duration of 50 ms. The sets of two different membrane patches were provided. The results are shown in FIGS. 17A and 17B. The standard deviation of laser induced amplitude of ion channel current was less than 12% for each set of output power. There was not observed any post activation effects. The effective peak temperature of activation was determined by the following procedure: A part of membrane patches were heated until a maximum ion channel current was achieved and this procedure was repeated. At room temperature membrane patches were activated by capsaicin. The laser stimulation was used to control when (and what percentage .about.100%) ion channels are opened. Laser induced ion current decreased and DC current increase until the laser induced current decreased to 0. For kinetic protocols pulse durations from 20 to 50 msec with 4 W out put power were applied.

Stimulation of C and A-delta terminals is a result of activation of heat sensitive ion channels and depolarization on cell membranes of the terminals. The research in this direction may determine what vanilloid receptors (VR1 or VRL1) are responsive for heat activation of C and A delta fibers. These receptors have different threshold temperatures and could be correspondingly linked to C or A-delta terminals. The monitoring of their thresholds and kinetics permits the diagnosing of peripheral pain syndromes and evaluation of analgesic drug action on C and A delta terminals.

Example of Application of Behavioral Test

Stimulation of C Fibers of Rats and Influence of Drug on Threshold of Stimulation Animals: Male Sprague-Dawley rats (258±20 g, Charles River Laboratories) were housed in a 12/12-hour light/dark environment and provided food and water ad libitum (n=24). Effort was made to minimize discomfort and reduce the number of animals used.

Step 1

Rats were lightly anesthetized with urethane (1000 mg/kg ip) and placed with minimal restraint on a heating pad to maintain their body temperature at 37° C. Rats were slightly restrained in plastic cone, head and neck of rat was free of restrain.

Step 2

Laser pulses beam 5 mm spot diameter, power 0.8 W power and 30 sec pulse duration were applied to the ears and nostrils of rats. The lasing was terminated immediately upon withdrawal of ear or nose to prevent tissue damage.

Step 3

Step 2 was repeated for left and right ears and left and right nostrils of rats. The stimulation site was changed after each long pulse allowing at least 2 minutes in between 2 stimuli on the same ear or nostril. The testing sessions were videotaped for precise measurement of response latencies.

Step 4

One of three drugs, Capsaicin, Morphine or Dimethyl Sulfoxide (DMSO) were applied for each rat. Thereafter, 5 mm, 0.8 W, 30 sec laser pulses were applied and response latencies were measured.

Description of applied drug: Capsaicin (10 mM, Sigma-Aldrich Co., St Louis, Mo., USA) was dissolved in 50% ethanol in $H_2O$ and applied to rats in group 1. Rats in group 2 received DMSO (dimethylsulfoxide, Sigma-Aldrich Co., St Louis, Mo., USA). Capsaicin and DMSO were applied to the ear with cotton tipped applicators. Rats in group 3 received an intramuscular injection of morphine (1 mg/kg, Lylly). Response latencies were re-tested 20 minutes after the drugs had been administered. Measured latencies were analyzed using NONMEM® (GloboMax LLC, Hanover, Md.).

Figure 18:
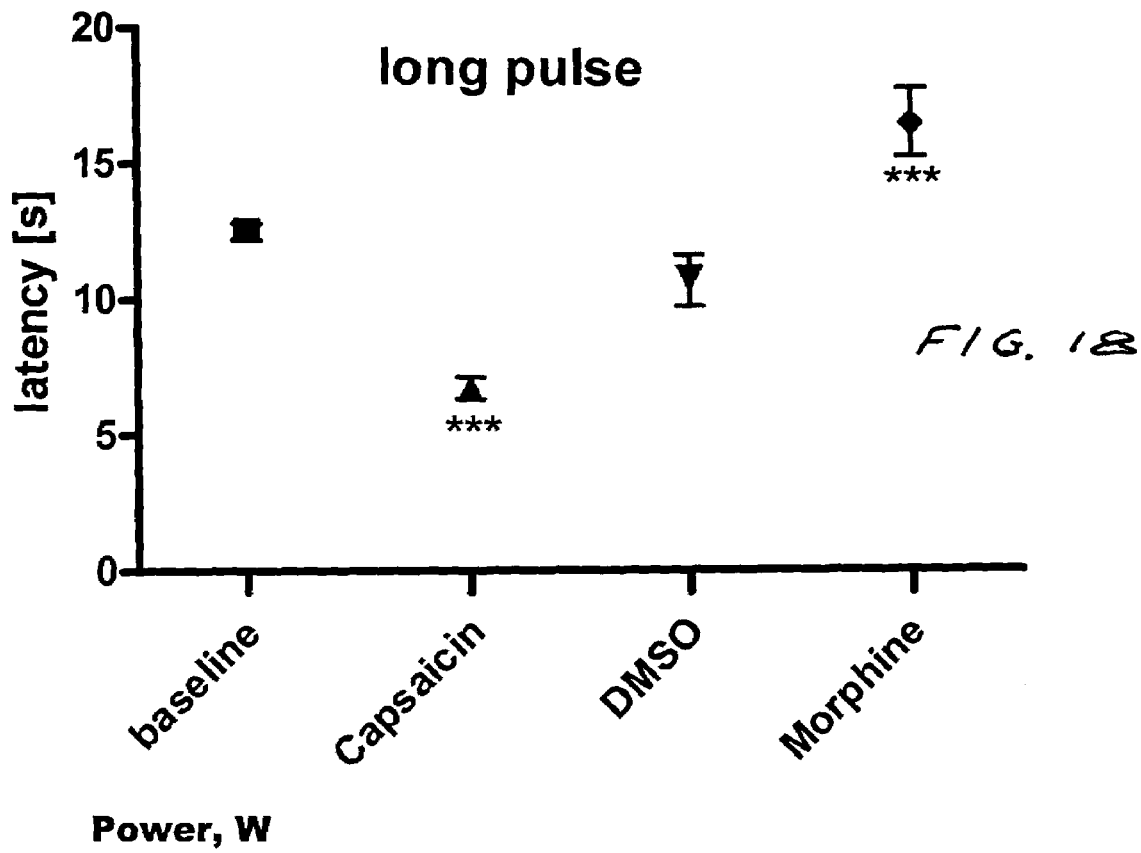
FIG. 18 shows results of drug action on C fiber stimulation in rats.

6 rats were tested with each drug. Results of behavioural test of rats of C fibers stimulation for each drug are shown in FIG. 18.

Example of Behavioral Tests

Application of Stimulation of A Delta Fibers of Rats and Influence of Drug on Threshold of Stimulation Animals: Male Sprague-Dawley rats (258±20 g, Charles River Laboratories) were housed in a 12/12-hour light/dark environment and provided food and water ad libitum (n=24). Effort was made to minimize discomfort and reduce the number of animals used.

Step 1

Rats were lightly anesthetized with urethane (1000 mg/kg ip) and placed with minimal restraint on a heating pad to maintain their body temperature at 37° C. Rats were slightly restrained in plastic cones, head and neck of rat were free of restraint Step 2

Laser beam pulses (2 mm spot diameter, duration 200 ms) were applied to the ears and nostrils of rats. Stimulation was started with output power well below the typical threshold of 0.5 W. After each short pulse the testing sites were alternated as well allowing at least 45 seconds in between 2 stimuli applied to the same ear. Step of increasing of power was 0.1 W The testing sessions were videotaped for precise measurement of latency time.

Step 3

Step 2 was repeated for left and right ears and left and right nostrils of rats. The stimulation site was slightly changed after each brief pulse allowing at least 45 sec in between 2 stimuli on the same ear or nostril. The testing sessions were videotaped for precise measurement of time.

Step 4

One of tree drugs, Capsaicin, Morphine or Dimethyl Sulfoxide (DMSO) were applied for each rat. Thereafter, 5 mm, 0.8 W, 30 sec laser pulses were applied and response latencies were measured.

Description of applied drug: Capsaicin (10 mM, Sigma-Aldrich Co., St Louis, Mo., USA) was dissolved in 50% ethanol in $H_2O$ and applied to rats in group 1. Rats in group 2 received DMSO (dimethylsulfoxide, Sigma-Aldrich Co., St Louis, Mo., USA). Capsaicin and DMSO were applied to the ear with cotton tipped applicators. Rats in group 3 received an intramuscular injection of morphine (1 mg/kg, Lylly). Response latencies were re-tested 20 minutes after the drugs had been administered. Measured latencies were analyzed using NONMEM® (GloboMax LLC, Hanover, Md.

Figure 19:
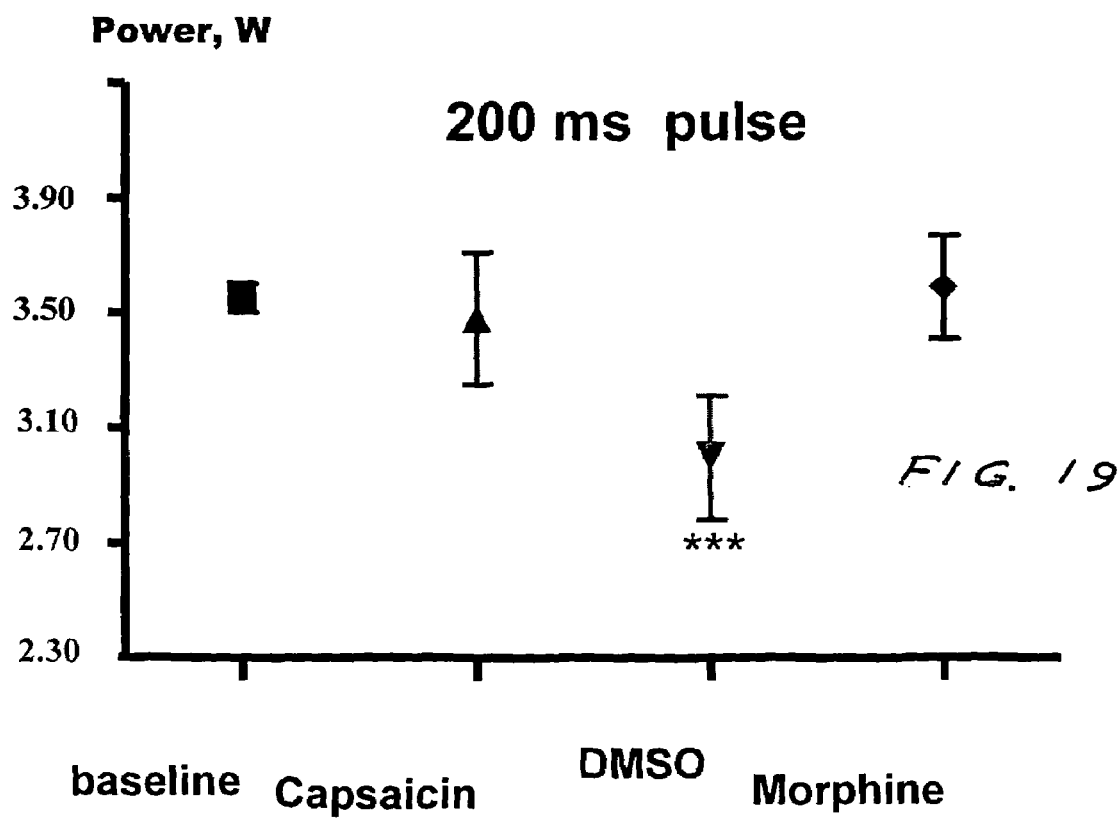
FIG. 19 shows results of drug action on A-delta fiber stimulation in rats.

Six rats were tested with each drug. Results of behavioral test of rats of A delta fibers stimulation for each drug are sown in FIG. 19.

Comparison Of In Viro and In Vitro Pain Results

This idea was experimentally tested when the adequate laser heat stimuli were applied in vivo to the skin of volunteer and in vitro using of the somata of dorsal root ganglion (DRG) neurons. The absorption of human and animal skin of near infrared light in the interval of 900-1600 nm is mostly determined by water absorption. Thus, the location of investigated cells from DRG as well as cell membrane patchs in water solution in depth close to the depths location of nociceptor terminals in the skin .about.300-600 microns can allow directly experimental comparison of activation by the same stimulation parameters of laser stimuli in vitro and in vivo.

General Algorithms

The following are examples of control algorithms useful in setting up the laser and optics for practicing the present invention:

1) Standard square wave laser pulses:

Laser single pulse: 1 ms-100 sec, Step 1 ms

Repeatable pulses 1 ms-100 sec with interval between pulses: 1 ms-2000 sec.

2) Arbitrary shape laser pulse built from 100 elements. Each element has a duration and initial and final current arbitrary shaped pulse that could be single or repeatable (see FIGS. 10, 11, 12, 13, 14, 15).

3) Each arbitrary and standard pulses regimes have Trigger In and Trigger Out synchronic pulses with tunable delay. For manual access to the device Trigger In option switch off for access via PC switch on. Trigger In and Out input and output have separate BNC connectors on back side of the device.

4) Aiming beam has fast driver Rise/fall time of green (red, blue) laser (diodes) better that 1 microseconds. Driver current of aiming beam—up to 300 mA. Voltage up to 5 V for blue laser. Switch off/on time is less than 1.0 microsecond. The power of aiming beam is of 0.5-10 mW.

5) Two ADC inputs are connected on the back panel through DB9 connector.

6) Control Voltage on Input Pulse Length Timer Stop (Pulse Length Timer Stop input (TTL, active high)) and input Stop the laser input (shuts down the laser) (TTL, active low) are located on back panel through a separate DB9 connector.

Every command has a description there is described of the aim of the command, parameters that command control and range of parameters i.e. Tmin; Tmax; Step—for pulse duration.

The set of command is for following:
a) arbitrary shape of pulses
b) measurement of number of applied pulses for repetitive pulses when lasing is terminated,
c) measurement of pulse duration of single pulses when lasing is terminated, and
d) reading all parameters of applied pulses: power, current, pulse shape, pulse duration, interstimulus intervals, trigger pulses delays, power of aiming beam, pulse duration of aiming beam.

While the present invention has been described in terms of specific embodiments, persons skilled in the art will recognize that many modifications and additions could be made to the specific embodiments without departing from the basic principals of the invention. For example many different wavelengths could be utilized if they the absorption in skin is within the range of about 0.25 $cm^{-1}$ to 10 $cm^{-1}$. Fiber optics with core diameters in the range of 5 to 100 microns are good for transmitting the laser pulses. Pulse shapes such as the following are good shapes for many experiments:

1. Increasing of power for pulse duration 50-150 ms from power level of 0.5 W with step less than 0.2 W with a diameter of irradiation area 0.5-2 mm lead to produce clear monomodal (single) pin prick pain and selective activation of A delta fibers.
2. Increasing of pulse duration from 0.3 to 20 sec with power level around 1.5 W with a diameter of irradiation area 5 mm-15 mm lead to inducing of clear monomodal hot pain and selective activation of C fibers.
3. Increasing of power for pulse duration of 400-500 ms with a diameter of irradiated area 3-5 mm may induce clear single hot pain or clear single warmth sensation and selective activation of C fibers.

Therefore, the scope of the invention should be determined by the appended claims and their legal equivalents.

What is claimed is:

1. A process for stimulating nerves for conducting nerve research and investigations, said process comprising:
    A) generating pulses of infrared light with a diode laser,
    B) controlling said laser to produce laser pulses of desired duration and power to produce a desired pulse power profile,
    C) directing at least a portion of said pulses of infrared light to a target comprising a single nerve or a portion of said single nerve so as to produce single mode stimulation of the nerve.

2. The process as in claim 1 wherein said infrared light is infrared light at wavelengths of about 980 nm.

3. The process as in claim 1 wherein said nerve fibers are C fiber nociceptors.

4. The process as in claim 3 and including a step of identifying the single type of stimulation as warmth stimulation.

5. The process as in claim 3 and including a step of identifying the single type of stimulation as single hot stimulation.

6. The process as in claim 1 wherein said nerve fibers are A-delta fiber nociceptors.

7. The process as in claim 6 and including a step of identifying the single type of stimulation as prick pin stimulation.

8. The process as in claim 1 wherein said controller comprises a personal computer.

9. The process as in claim 1 and further comprising a step for sensing temperature of said target.

10. The process as in claim 9 wherein said temperature sensor is configured to provide a temperature signal to said controller and said controller is programmed to utilize said temperature to provide feedback control of said laser in order to provide a desired temperature profile at said target.

11. The process as in claim 1 wherein said controller is programmed to provide laser pulsed according to a predetermined pulse energy profile to produce pain but no tissue injury.

12. The process of claim 1 and further comprising the steps of increasing of power for pulse duration 50-150 ms from power level of 0.5 W with step less than 0.2 W with a diameter of irradiation area 0.5-2 mm lead to produce clear monomodal (single) pin prick pain and selective activation of A delta fibers.

13. The process of claim 1 and further comprising the steps of increasing of pulse duration from 0.3 to 20 sec with power level around 1.5 W with a diameter of irradiation area 5 mm-15 mm lead to inducing of clear monomodal hot pain and selective activation of C nociceptors.

14. The process as in claim 1 and including a step of identifying the single type of nerve as a single nerve cell.

15. The process as in claim 1 wherein the said infrared light is directed to said target using an optical fiber with a core diameter chosen from a group of diameters consisting of:
    20+/−15 microns,
    60+/−15 microns and
    100+/−15 microns.

16. The process as in claim 1 wherein said infrared light is infrared light having a wavelength of about 1450 nm.

17. The process as in claim 1 wherein said infrared light is infrared light having a wavelength of about 1850 nm.

18. The process as in claim 1 wherein said infrared light is infrared light having a wavelength of about 810 nm.

* * * * *